United States Patent
Minai et al.

(10) Patent No.: US 7,509,158 B2
(45) Date of Patent: Mar. 24, 2009

(54) SYSTEM FOR DETECTING POSITION OF CAPSULE ENDOSCOPE IN SUBJECT

(75) Inventors: Tetsuo Minai, Tokyo (JP); Hatsuo Shimizu, Tokyo (JP)

(73) Assignee: Olympus Corporation, Tokyo (JP)

( * ) Notice: Subject to any disclaimer, the term of this patent is extended or adjusted under 35 U.S.C. 154(b) by 410 days.

(21) Appl. No.: 11/020,441

(22) Filed: Dec. 23, 2004

(65) Prior Publication Data
US 2005/0143643 A1 Jun. 30, 2005

(30) Foreign Application Priority Data
Dec. 26, 2003 (JP) ............................. 2003-435555

(51) Int. Cl.
*A61B 3/16* (2006.01)
(52) U.S. Cl. ..................... 600/424; 600/407; 600/410; 600/411; 600/425; 600/160; 600/109
(58) Field of Classification Search ................. 600/407, 600/424, 426, 160, 101, 410, 411, 425, 109
See application file for complete search history.

(56) References Cited

U.S. PATENT DOCUMENTS

| 5,681,260 | A | 10/1997 | Ueda et al. | |
|---|---|---|---|---|
| 6,833,814 | B2 * | 12/2004 | Gilboa et al. | 342/448 |
| 7,076,284 | B2 * | 7/2006 | Segawa et al. | 600/424 |
| 2002/0173718 | A1 * | 11/2002 | Frisch et al. | 600/424 |
| 2003/0229268 | A1 * | 12/2003 | Uchiyama et al. | 600/109 |
| 2004/0111011 | A1 * | 6/2004 | Uchiyama et al. | 600/160 |
| 2004/0138552 | A1 * | 7/2004 | Harel et al. | 600/407 |
| 2004/0204630 | A1 * | 10/2004 | Gilad | 600/160 |
| 2004/0254455 | A1 * | 12/2004 | Iddan | 600/424 |
| 2006/0224063 | A1 * | 10/2006 | Segawa et al. | 600/424 |

FOREIGN PATENT DOCUMENTS

| JP | 4-8341 | 1/1992 |
|---|---|---|
| JP | 09-028662 | 2/1997 |
| JP | 9-94257 | 4/1997 |
| JP | 2003-019111 | 1/2003 |
| JP | 2003-117004 | 4/2003 |

* cited by examiner

*Primary Examiner*—Brian L. Casler
*Assistant Examiner*—Sanjay Cattungal
(74) *Attorney, Agent, or Firm*—Scully, Scott, Murphy & Presser, P.C.

(57) ABSTRACT

A system includes a device that is swallowed, passed through a subject, and includes a magnetic field generator generating a constant magnetic field; and a position transducer. The position transducer includes a plurality of magnetic detectors detecting intensities of a magnetic filed, first and second fixing units that fix at least one magnetic detector to the subject, respectively, a position fluctuation detector that detects a fluctuation of positional relation between the first fixing unit and the second fixing unit, a coordinate calibrating unit that calibrates position coordinate of the magnetic detector based on a detection result by the position fluctuation detector. The system also includes a position processor that calculates a position of the device in the subject based on an intensity of the constant magnetic field detected by the magnetic detector and the position coordinate of the magnetic detector after calibration by the coordinate calibrating unit.

13 Claims, 15 Drawing Sheets

SYSTEM FOR DETECTING POSITION OF CAPSULE ENDOSCOPE IN SUBJECT

CROSS-REFERENCE TO RELATED APPLICATIONS

This application claims the benefit of priority of Japanese Patent Application No. 2003-435555 filed in Japan on Dec. 26, 2003, and the disclosure of which is incorporated herein by its entirety.

BACKGROUND OF THE INVENTION

1. Field of the Invention

The present invention relates to a system for detecting a position of a device such as a capsule endoscope, which is swallowed and passes naturally through the digestive tract of the subject, by a position transducer that is disposed on the outside of the subject and obtains information of the position of the device in the subject.

2. Description of the Related Art

In recent years, in the field of endoscopes, a swallowable capsule endoscope has been proposed. The capsule endoscope has an image capturing function and a radio communication function. The capsule endoscope has the function of traveling in the body cavity, for example, in the organs such as the stomach and the small intestine with peristalsis of the organs and sequentially capturing images for a period of time since the capsule endoscope is swallowed from the mouth of a subject for inspection (examination) until it is naturally excreted.

Image data captured in the body by the capsule endoscope as the capsule endoscope travels in the body cavity is sequentially transmitted by radio communication to the outside and stored into a memory provided on the outside. The subject can freely move throughout the period after he/she swallows the capsule endoscope until it is excreted by carrying a receiver having a radio communication function and a storing function. After the capsule endoscope is excreted, a doctor or nurse can display the images of the organs on a display based on the image data stored in the memory and make a check.

A capsule endoscope has been proposed in which the receiver has the function of detecting the position of the capsule endoscope in the subject to capture, for example, an endoscope image of a specific organ in the subject. As an example of a capsule endoscope system having the position detecting function, a capsule endoscope system using the radio communication function provided in the capsule endoscope is known. Specifically, the system has a configuration that a receiver provided on the outside of a subject has a plurality of antenna elements, and has the function of receiving a radio signal transmitted from the capsule endoscope by the plurality of antenna elements and, based on intensities received by the antenna elements, detecting the position of the capsule endoscope in the subject (see Japanese Patent Application Laid-open No. 2003-19111, for example).

SUMMARY OF THE INVENTION

It is an object of the present invention to at least solve the problems in the conventional technology.

A system according to one aspect of the present invention includes a device that is swallowed, passed through a subject, and includes a magnetic field generator generating a constant magnetic field; and a position transducer. The position transducer includes a plurality of magnetic detectors detecting intensities of a magnetic filed, a first fixing unit that fixes at least one magnetic detector to the subject, a second fixing unit that fixes at least one magnetic detector to the subject, a position fluctuation detector that detects a fluctuation of positional relation between the first fixing unit and the second fixing unit, a coordinate calibrating unit that calibrates position coordinate of the magnetic detector based on a detection result by the position fluctuation detector, and a position processor that calculates a position of the device in the subject based on an intensity of the constant magnetic field detected by the magnetic detector and the position coordinate of the magnetic detector after calibration by the coordinate calibrating unit.

The other objects, features, and advantages of the present invention are specifically set forth in or will become apparent from the following detailed description of the invention when read in conjunction with the accompanying drawings.

DETAILED DESCRIPTION

Figure 1:
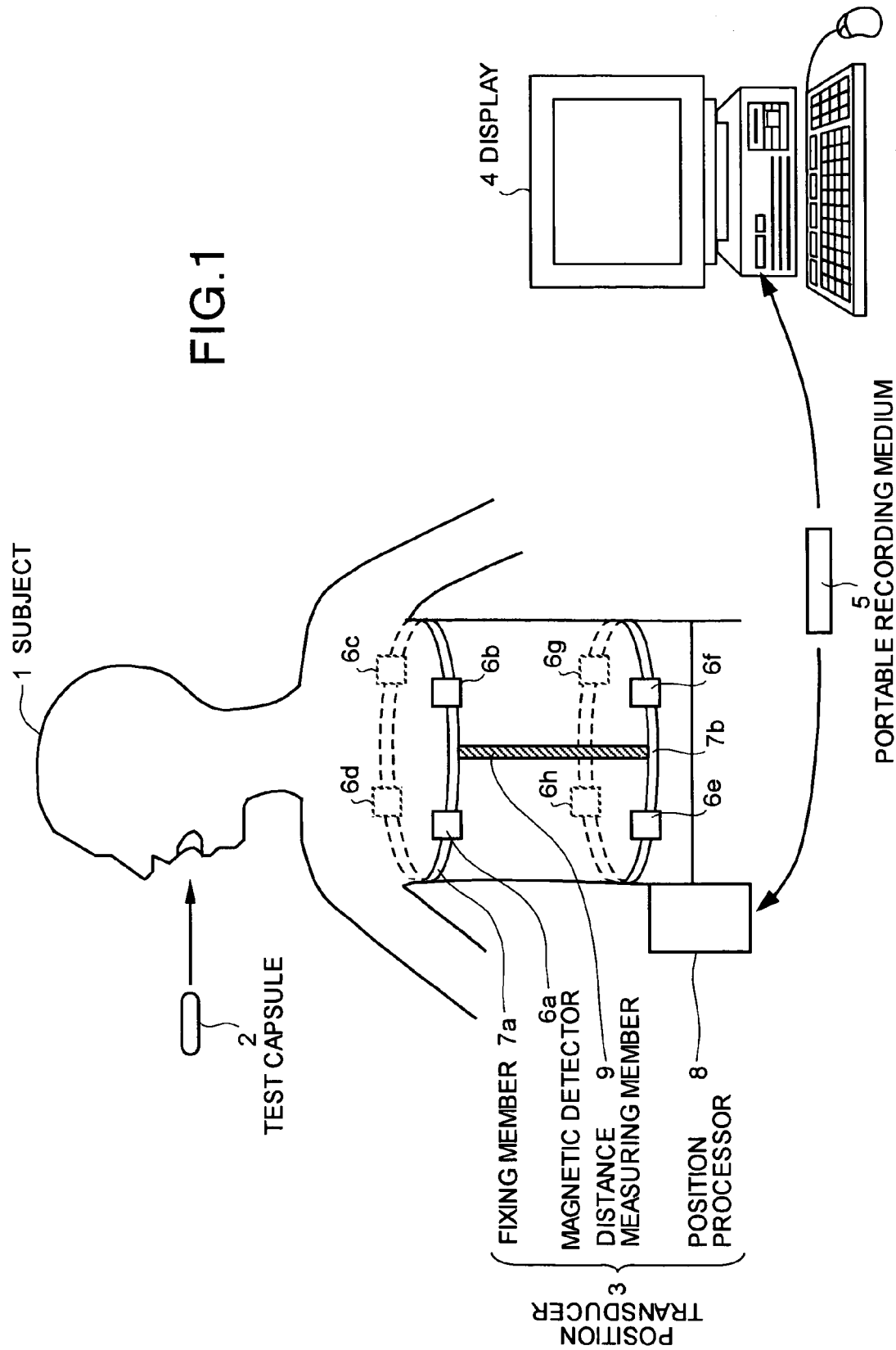
FIG. 1 is a schematic view of a system for detecting a position of a capsule endoscope in a subject according to a first embodiment.

Exemplary embodiments of a system for detecting a position of a capsule endoscope in a subject relating to the present invention will be explained in detail below with reference to the accompanying drawings. It should be noted that the drawings are schematic ones and the relation between thickness and width of each part, the thickness ratio of the parts, and the like are different from real ones. Obviously, the drawings include parts having different relations of dimensions and ratios.

A system for detecting a position of a capsule endoscope in a subject according to a first embodiment will now be explained. The system for detecting a position of a capsule endoscope according to the first embodiment of the present invention includes a test capsule 2 that is swallowed and passes though a subject 1 and functions as an example of a device to be traveled in a subject; a position transducer 3 that detects the position in the subject 1 of the test capsule 2; a display 4 displaying position information of the test capsule 2 detected by the position transducer 3; and a portable recording medium 5 for transmitting/receiving information between the position transducer 3 and the display 4.

The display 4 is used for displaying position information of the test capsule 2 obtained by the position transducer 3 and has a configuration like a workstation or the like that displays an image based on data obtained from the portable recording medium 5. Concretely, the display 4 may be constructed to directly display an image by a cathode-ray tube (CRT) display, a liquid crystal display, or the like or to output an image to another medium like a printer or the like.

The portable recording medium 5 can be inserted/removed to/from a position processor 8 that is explained later and the display 4, and has a structure capable of outputting and recording information when inserted to the position processor 8 and the display 4. Concretely, the portable recording medium 5 is inserted in the position processor 8 to record information on the position of the test capsule 2 while the test capsule 2 travels in the body cavity of the subject 1. After the test capsule 2 is excreted from the subject 1, the portable recording medium 5 is removed from the position processor 8 and inserted into the display 4, and the recorded data is read by the display 4. By transmitting data between the position processor 8 and the display 4 by the portable recording medium 5 such as a compact flash (trademark) memory, different from the case where the position processor 8 and the display 4 are connected to each other by wire, even when the test capsule 2 is traveling in the subject 1, the subject 1 can move freely.

The test capsule 2 is used at the time of conducting a preliminary inspection to check whether or not a narrow part in which passage of a capsule endoscope is difficult exists in the subject 1 before introduction of the capsule endoscope or the like into the subject 1. The system according to the first embodiment is used to check how the test capsule 2 travels in the subject 1. To achieve the purpose, a high-precision position detecting mechanism is provided.

Figure 2:
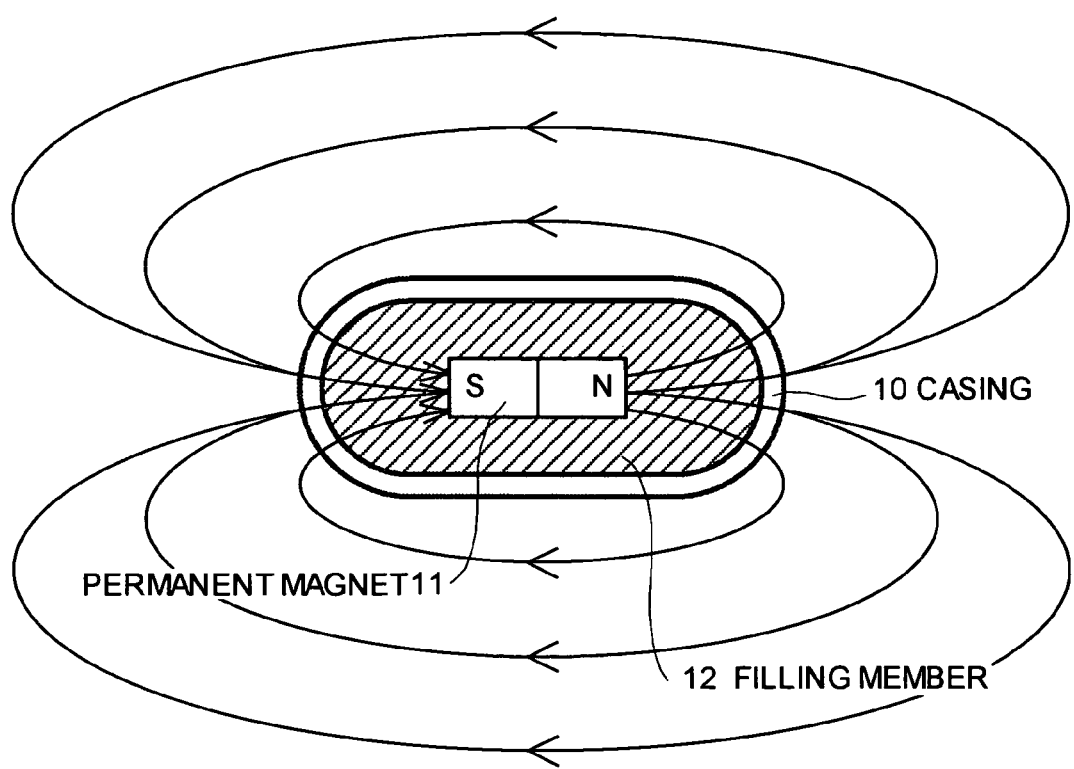
FIG. 2 is a schematic view of a test capsule as a component of the system according to the first embodiment.

FIG. 2 is a schematic diagram of the test capsule 2. As shown in FIG. 2, the test capsule 2 includes a casing 10 having a capsule shape that is similar to that of a casing of a capsule endoscope; a permanent magnet 11 disposed in the casing 10; and a filling member serving to fill the clearance between the inner surface of the casing 10 and the permanent magnet 11.

The casing 10 is made of, for example, a bio-compatible material and has a characteristic such that when the casing 10 remains in the subject 1 for a few days, the material dissolves. By forming the casing 10 of a bio-compatible material, there is an advantage such that even if the test capsule 2 introduced in the subject 1 is not excreted to the outside of the subject 1, it is unnecessary to perform an abdominal operation or the like on the subject 1.

The permanent magnet 11 functions as a constant magnetic field generator in the claims, has a size that can be housed in the casing 10, and is to output a constant magnetic field whose intensity fluctuation with time is ignorable. In place of the permanent magnet 11, for example, a coil that receives constant current and generates a constant magnetic field may be used as the constant magnetic field generator. In the case of using the permanent magnet 11, there is an advantage such that drive power is unnecessary. Thus, it is preferable to construct the constant magnetic field generator by using the permanent magnet 11.

As shown in FIG. 2, the constant magnetic field generated from the permanent magnet 11 is expressed by a line of magnetic force of a closed curve that is output from the N pole side, travels on the outside of the permanent magnet 11, and enters again on the S pole side. As shown in FIG. 2, the travel direction of the line of magnetic force has location dependency but it can be regarded that the intensity of the constant magnetic field expressed by the line of magnetic force is determined only in accordance with the distance from the test capsule 2. Specifically, the size of the permanent magnet 11 provided in the test capsule 2 is small enough to be ignored as compared with the distance between the test capsule 2 and magnetic detectors 6a to 6h. Consequently, magnetic field intensity P at a point apart from the test capsule 2 only by distance "r" is expressed as follows by using a proportional factor α.

$$P = \alpha/r^3 \quad (1)$$

The system according to the first embodiment detects the position of the test capsule 2 based on the relation shown in Equation (1) as is explained later.

The filling member 12 is provided to fill the clearance between the inner face of the casing 10 and a permanent magnet 11 to fix the position of the permanent magnet 11. The material of the filling member 12 does not exert an adverse influence on the subject 1. For example, the filling member 12 is made of barium sulfate. Since barium sulfate can be used as a contrast medium in an X-ray inspection, position detection by an X-ray inspection can be performed in addition to the position detection of the first embodiment. By comparing the results of both of the inspections, more accurate position detection can be performed. Obviously, it is not essential to use barium sulfate as the filling member 12 in the first embodiment and an arbitrary material can be used as long as the material functions as the filling member.

The position transducer 3 is explained. The position transducer 3 detects the position of the test capsule 2 in the subject 1 based on the constant magnetic field output from the test capsule 2. Concretely, the position transducer 3 has, as shown in FIG. 1, the magnetic detectors 6a to 6h for detecting the intensity of the constant magnetic field output from the test capsule 2, a fixing member 7a for fixing the magnetic detectors 6a to 6d to the subject 1, a fixing member 7b for fixing the magnetic detectors 6e to 6h to the subject 1, the position processor 8 for calculating the position of the test capsule 2 based on the magnetic field intensities detected by the magnetic detectors 6a to 6h and the distance measuring member for detecting variation of distance between fixing members 7a and 7b.

Each of the magnetic detectors 6a to 6h is to detect the magnetic field intensity in the position where it is disposed. More specifically, each of the magnetic detectors 6a to 6h is constructed by a Magneto Impedance (MI) sensor, for example. The MI sensor has a configuration using, for example, an FeCoSiB amorphous wire as a magneto-sensitive medium and senses the magnetic field intensity by using an MI effect that the magnetic impedance of the magneto-sensitive medium largely changes according to an external magnetic field when high-frequency current is passed to the magneto-sensitive medium. The magnetic detectors 6a to 6h may be constructed by other magnetic sensors, though the MI sensor provides particularly highly sensitive magnetic intensity detection. The magnetic detectors 6a to 6d are disposed in positions at vertexes of a square whose side has length "a" and the magnetic detectors 6e to 6h are disposed similarly.

The fixing member 7a functions in a mode of a first fixing unit in the claims and the fixing member 7b functions in a mode of a second fixing unit in the claims. Concretely, each of the fixing members 7a and 7b is formed in an annular shape so as to surround the trunk of the subject 1 and is fixed in a state where it is closely attached to the trunk of the subject 1. The magnetic detectors 6a to 6d and the magnetic detectors 6e to 6h are fixed to predetermined positions in the subject 1 by the fixing members 7a and 7b, respectively. As a result, the positional relations among the magnetic detectors 6a to 6h are fixed, and the positional relations among the magnetic detectors 6e to 6h are also fixed. In the first embodiment, from the viewpoint of lessening the burden of position calibration of the magnetic detector, the fixing member 7b is fixed to a region in which no positional fluctuation occurs even when the subject 1 moves. In the first embodiment, irrespective of the motion or the like of the subject 1, the position of the fixing member 7b does not fluctuate, and the positions of the magnetic detectors 6e to 6h fixed to the fixing member 7b do not also fluctuate.

The distance measuring member 9 functions in a mode of a distance measuring unit in the claims and is used to construct the position fluctuation detector in the claims in cooperation with a position fluctuation calculator 21 that is explained later. Concretely, the distance measuring member 9 is disposed in a state where both ends are fixed to predetermined points on the fixing members 7a and 7b and its length fluctuates according to fluctuations in the posture of the subject 1 or the like. The distance measuring member 9 also has the mechanism of detecting the range of variation in the length of itself, that is, the range of variation in the distance between the both ends of itself. By the detecting mechanism, the distance between the predetermined points on the fixing members 7a and 7b is derived.

Figure 3:
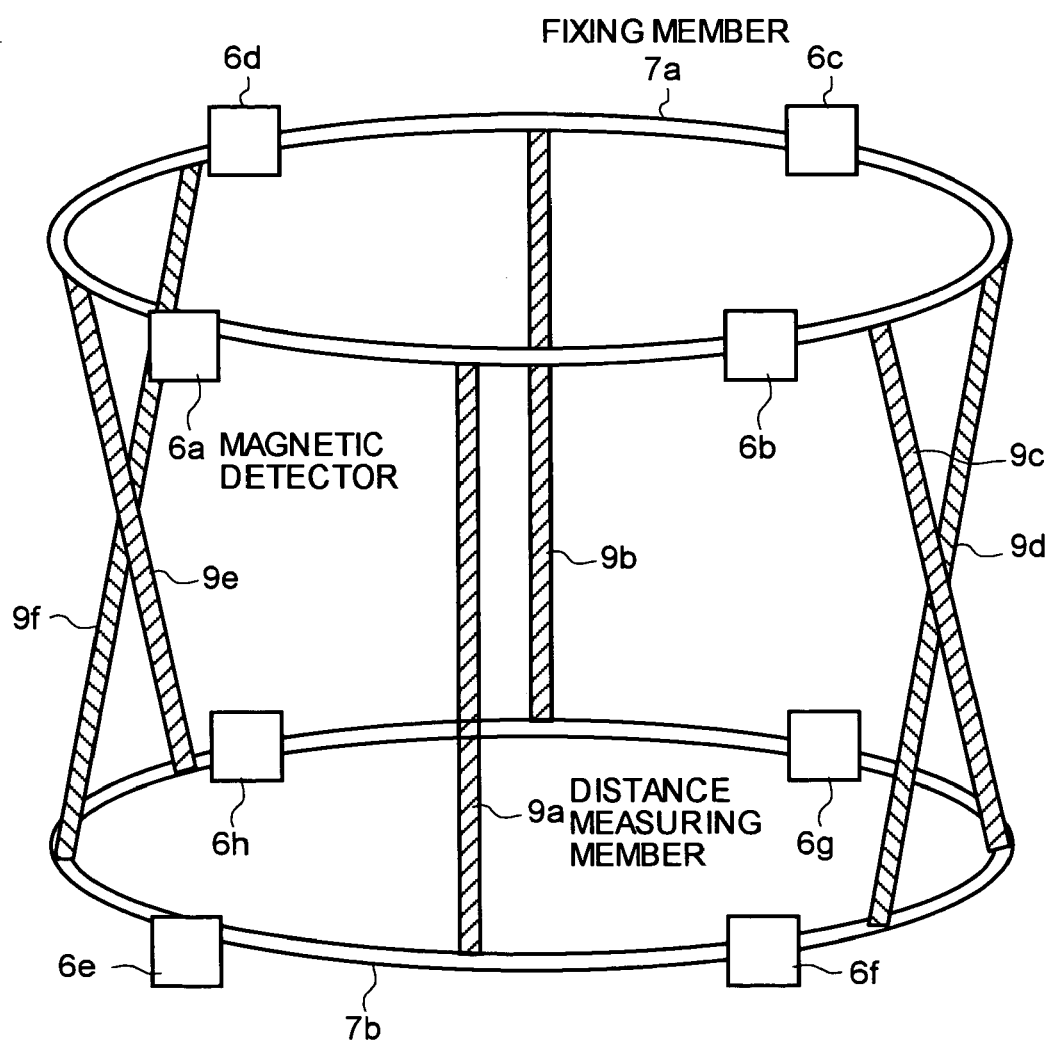
FIG. 3 is a schematic view of an arrangement of a distance measuring member as a component of the system according to the first embodiment.

FIG. 3 is a schematic view that depicts an example of an arrangement of the distance measuring member 9. As shown in FIG. 3, the position transducer 3 includes a distance measuring member 9a disposed so as to be positioned in the front of the subject 1 when the fixing members 7a and 7b are attached to the subject 1; a distance measuring member 9b disposed so as to be positioned on the back; distance measuring members 9c and 9d disposed so as to be positioned in a left-side face; and distance measuring members 9e and 9f disposed so as to be positioned in a right-side face. The distance measuring members 9c and 9d are disposed so as to cross each other to detect a twisting motion of the subject 1 that is explained later, and the distance measuring members 9e and 9f are disposed similarly.

Figure 4:
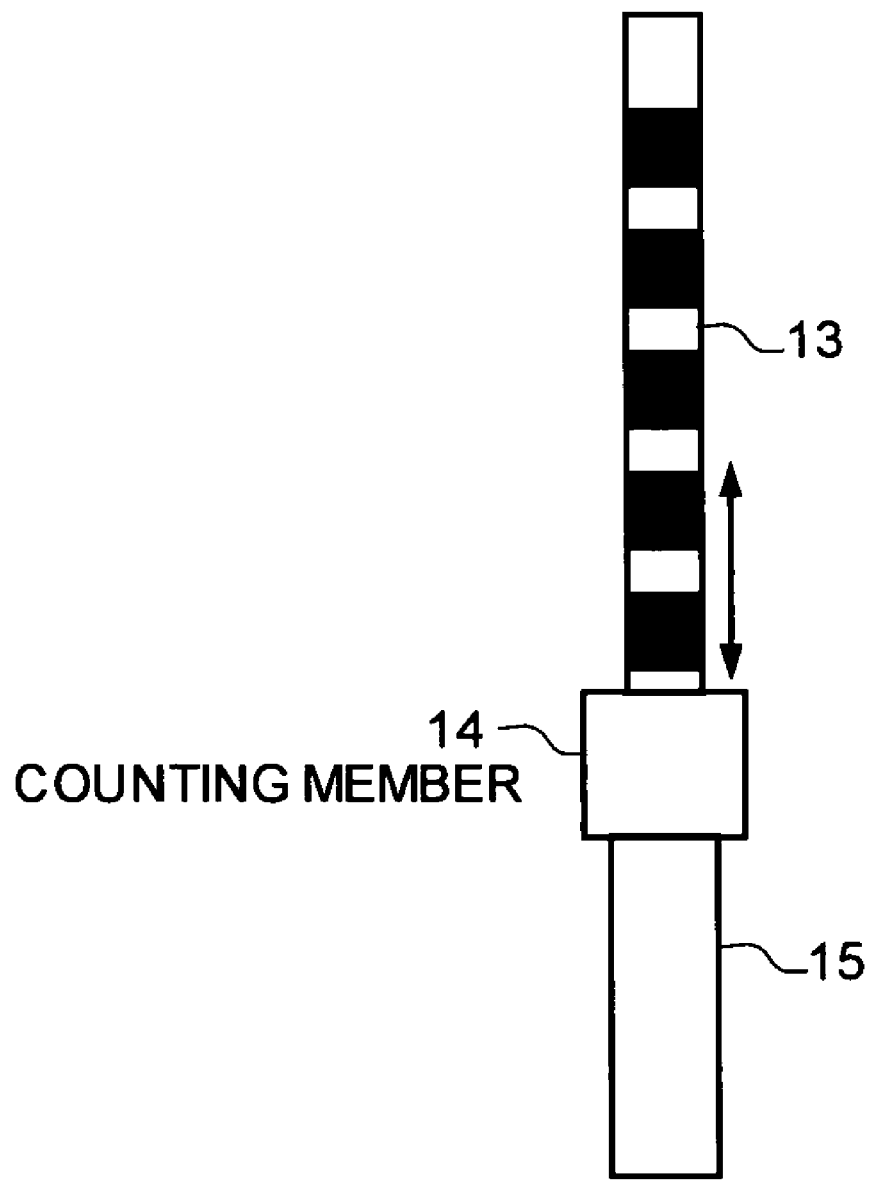
FIG. 4 is a schematic view of the distance measuring member.

FIG. 4 is a schematic view of an example of a concrete configuration of the distance measuring member 9. As shown in FIG. 4, the distance measuring member 9 includes a member 13 to be housed whose one end is fixed to a predetermined point in the fixing member 7a; a housing member 15 whose one end is fixed to a predetermined point in the fixing member 7b and having a structure housing the member 13 to be housed on the other end side; and a counting member 14 disposed on the side of housing the member 13 to be housed in the housing member 15 and having the function of detecting the length of the housed portion of the member 13.

The member 13 is formed by a member that easily curves according to a change in the posture or the like of the subject 1 like a plastic thin plate, and a pattern in which black and white regions each having a predetermined width are alternately arranged in the longitudinal direction is formed on the surface of the member 13. The member 13 is formed by the member that easily curves so as to suppress hindrance to the motion of the subject 1. The black and white pattern is formed on the surface to detect a distance fluctuation value by the counting member 14.

The counting member 14 has the function of reading the pattern formed on the surface of the member 13. Concretely, by counting the number of white patterns or black patterns passing a reading mechanism provided in the counting member 14, the fluctuation amount of the length of the portion housed in the housing member 15 of the member 13 is detected, and the detected fluctuation amount is output as a fluctuation value of the distance between two points at which the distance measuring members 9 are disposed.

The function of detecting a position fluctuation state between the fixing members 7a and 7b by using the distance measuring members 9a to 9f will now be concretely described. As movements of the subject 1, a bending motion such as forward bending and a twisting motion around the backbone as a rotation axis are mainly considered. In the following, detection of a position fluctuation state when the subject 1 bends and detection of a position fluctuation state when the subject 1 twists are explained.

Figure 5:
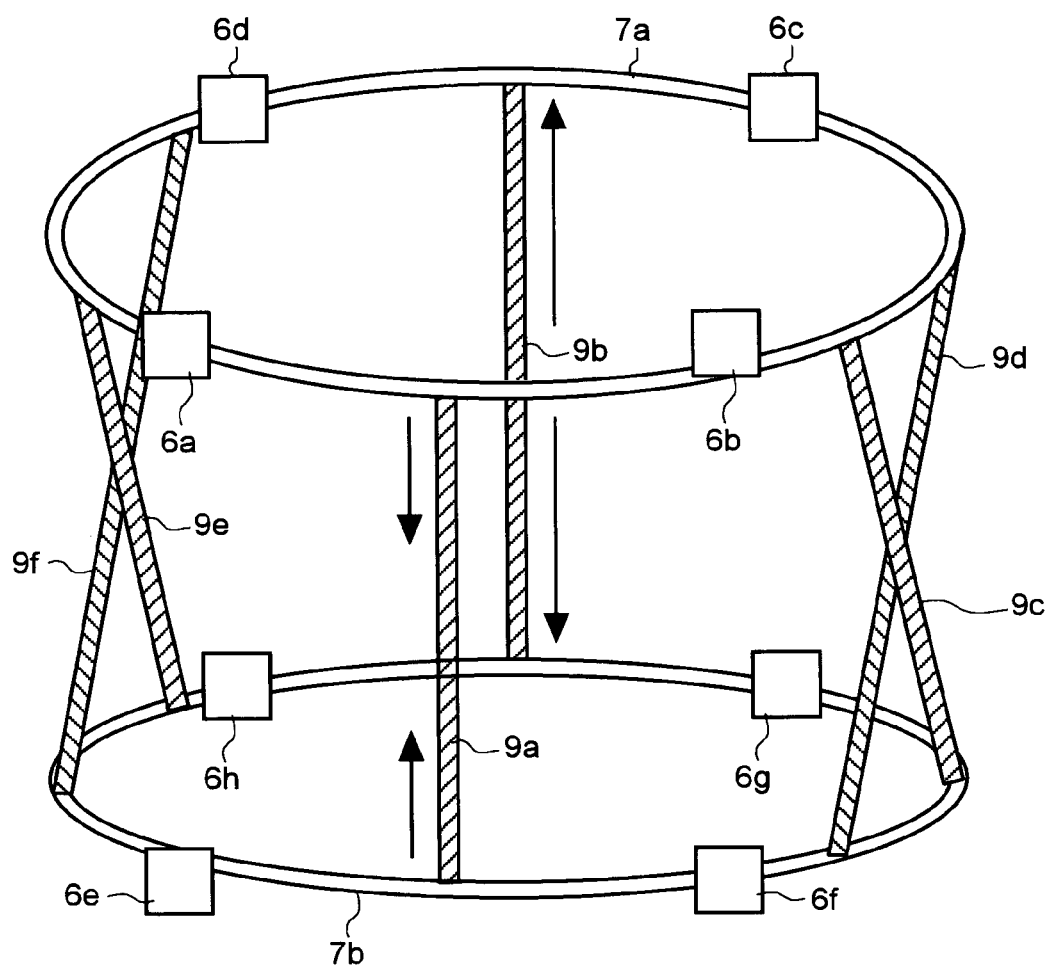
FIG. 5 is a schematic view of the distance measuring member when a subject bends.

FIG. 5 is a schematic view of the function of detecting the position fluctuation state when the subject 1 bends forward as an example of the bending motion. As shown in FIG. 5, when the subject 1 bends forward, the length of the distance measuring member 9a positioned in the front of the subject 1 at the time of attachment is reduced. On the other hand, the length of the distance measuring member 9b positioned at the back of the subject 1 increases. A distance decrease value and a distance increase value are detected, respectively. On the basis of the detection values, the position fluctuation amounts between the fixing members 7a and 7b are derived by the position fluctuation calculator 21 that is explained later.

Figure 6:
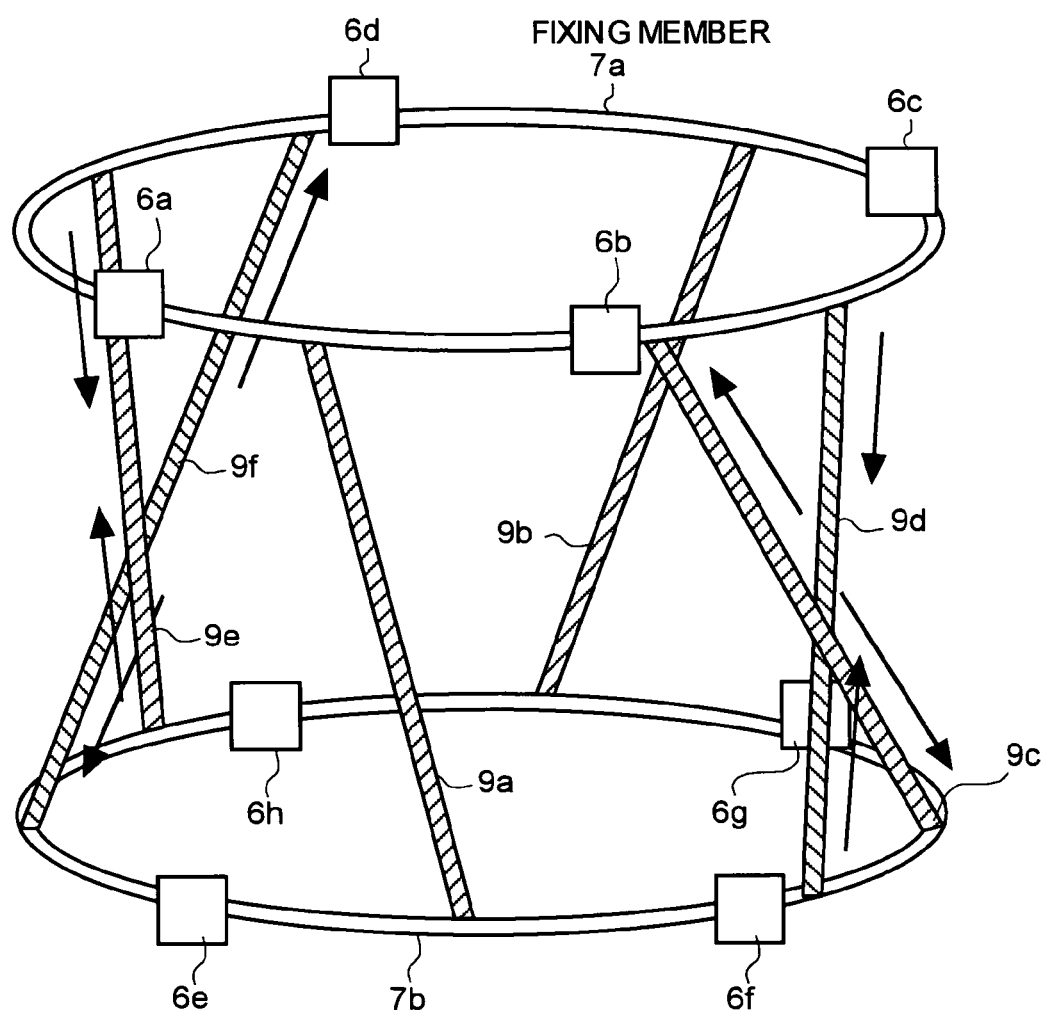
FIG. 6 is schematic view of the distance measuring member when a subject twists.

FIG. 6 is a schematic view of the function of detecting a position fluctuation state when the subject 1 twists in the clockwise direction when seen from above in the vertical direction. As shown in FIG. 6, when the subject 1 twists in the clockwise direction, the distance measuring members 9c and 9d positioned in the left-side face of the subject 1 at the time of attachment move differently from each other. Specifically, when the subject 1 twists in the clockwise direction, the fixing member 7a turns clockwise relative to the fixing member 7b. In correspondence with the turning motion, the length of the distance measuring member 9c increases whereas the length of the distance measuring member 9d decreases. Such changes similarly occur in the right-side face of the subject 1. In correspondence with the turn of the fixing member 7a, the length of the distance measuring member 9e is reduced whereas the length of the distance measuring member 9f increases. Although not shown, when the fixing member 7a turns counterclockwise relative to the fixing member 7b, for example, the length of the distance measuring member 9c decreases and the length of the distance measuring member 9d increases. The position fluctuation calculator 21 that is explained later derives the position fluctuation amount between the fixing members 7a and 7b based on variations in the fluctuation values of the distances detected by the distance measuring members 9a to 9f.

Figure 7:
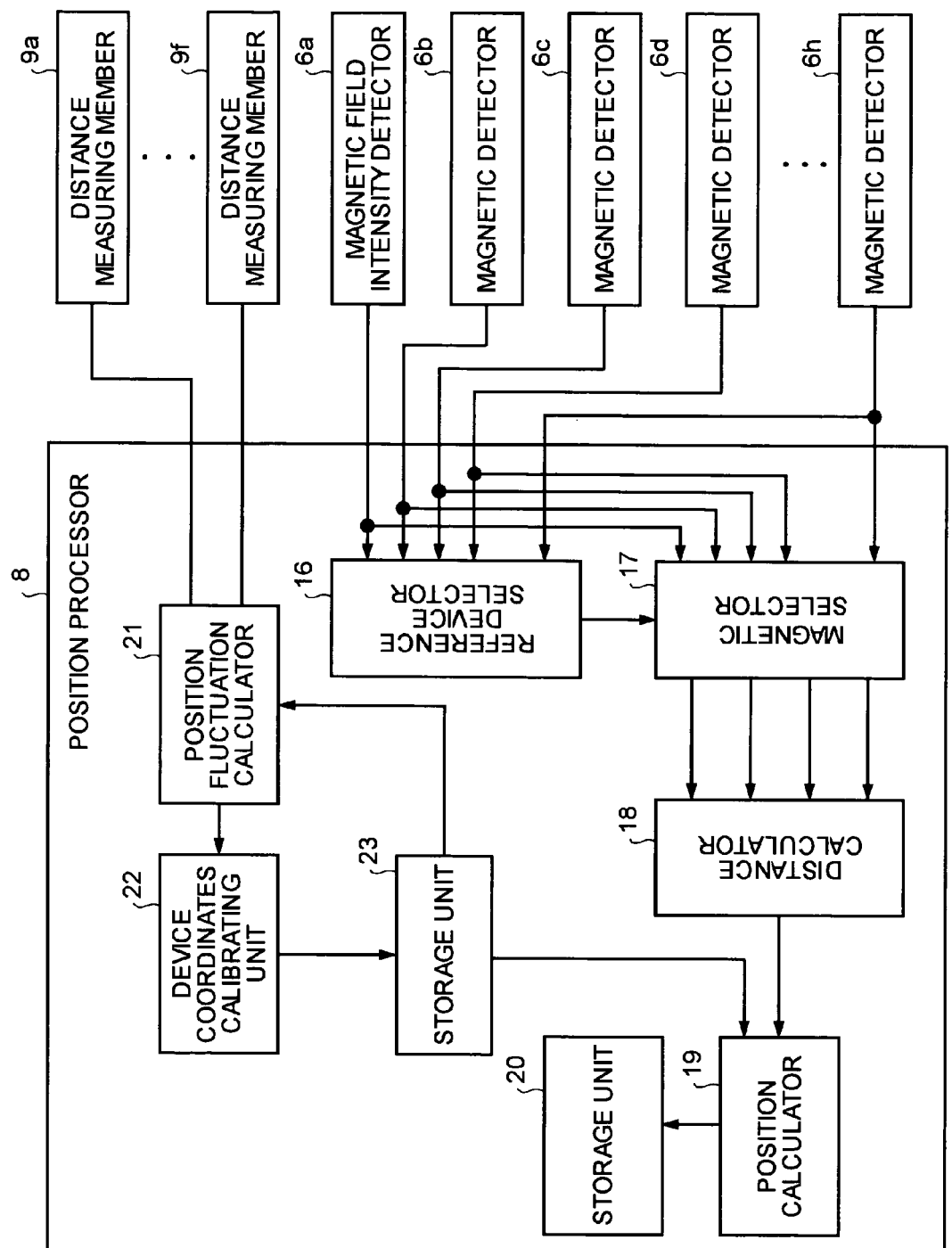
FIG. 7 is a schematic view of a position processor as a component of the system according to the first embodiment.

The position processor 8 is explained. The position processor 8 calculates the position of the test capsule 2 based on the magnetic field intensities sensed by the magnetic detectors 6a to 6h. A concrete configuration of the position, processor 8 is as shown in the block diagram of FIG. 7. As shown in FIG. 7, the position processor 8 includes a reference device selector 16 that selects a reference magnetic detector (hereinbelow, called "reference device") from the magnetic detectors 6a to 6h, and a magnetic selector 17 that outputs the magnetic field intensity obtained by the predetermined number of magnetic detectors based on the result of selection by the reference device selector 16. The position processor 8 includes a distance calculator 18 for calculating distance between the test capsule 2 and the reference device or the like based on the magnetic field intensity output from the magnetic selector 17; a position calculator 19 for calculating the position of the test capsule 2 by performing a computing process using the calculated distance and position coordinates of the reference device or the like used for calculating the distance; and a storage unit 20 for storing information of the position of the test capsule 2 obtained by the position calculator 19 into the portable recording medium 5. The position processor 8 also has: the position fluctuation calculator 21 that derives a position fluctuation amount between the fixing members 7a and 7b based on results of detection by the distance measuring members 9a to 9f; a device coordinates calibrating unit 22 that calibrates position coordinates of the magnetic detectors 6a to 6d based on a result of derivation by the position fluctuation calculator 21; and a storage unit 23 that stores the calibrated position coordinates of the magnetic detectors 6a to 6d.

The reference device selector 16 has the function of selecting the magnetic detector with the largest value of the detected magnetic field intensity from the magnetic detectors 6a to 6h. Concretely, the reference device selector 16 compares the magnetic field intensity values output from the magnetic detectors 6a to 6h with each other, selects the magnetic detector (reference device) that has output the largest magnetic field intensity value, and outputs information specifying the reference device (for example, information indicating the reference device among the magnetic detectors 6a to 6h) to the magnetic selector 17.

The magnetic selector 17 selects a plurality of magnetic detectors based on the result of selection of the reference device selector 16 and outputs the magnetic field intensities obtained by the selected magnetic detectors (selected devices) to the distance calculator 18. Concretely, the magnetic selector 17 has the function of selecting three magnetic detectors disposed in directions orthogonal to each other with respect to the reference device. Specifically, in the system according to the first embodiment, as also shown in FIG. 1, the magnetic detectors 6a to 6h are disposed so as to form vertexes of a cube, so that three magnetic detectors positioned in direction orthogonal to each other always exist for an arbitrary magnetic detector, and the magnetic selector 17 has the function of selecting the three magnetic detectors as selected devices.

The distance calculator 18 calculates the distances among the reference device, the selected devices, and the test capsule 2 based on the magnetic field intensities received via the magnetic selector 17. Concretely, the distance calculator 18 has the function of calculating the distance between the magnetic detector that has detected the magnetic field intensity and the test capsule 2 by performing the computing process shown by Equation (1) with respect to the input magnetic field intensity.

The position calculator 19 derives the position of the test capsule 2 by performing a predetermined computing process based on the distance between the magnetic detectors 6a to 6h selected as the reference device and the like and the test capsule 2 and the position coordinates of the magnetic detectors 6a to 6h obtained by the device coordinates calibrating unit 22 that is explained later. The position calculator 19 also has the function of outputting the result of derivation to the storage unit 20 after deriving the position of the test capsule 2.

The position fluctuation calculator 21 derives the fluctuation amount of the positional relation between the fixing members 7a and 7b based on results of detection by the distance measuring members 9a to 9f. Concretely, the position fluctuation calculator 21 derives the fluctuation amount of the positional relation between the fixing members 7a and 7b by correcting a three-dimensional stereomodel constructed by the fixing members 7a and 7b and the distance measuring members 9a to 9f when the subject 1 is in a basic posture based on the fluctuation values of the distances detected by the distance measuring members 9a to 9f when the subject 1 moves.

The device coordinates calibrating unit 22 functions in a mode of a coordinates calibrator in the claims. Concretely, the device coordinates calibrating unit 22 has the function of calibrating the position coordinates of the magnetic detectors 6a to 6h fixed on the fixing members 7a and 7b based on the fluctuation amount of the positional relation between the fixing members 7a and 7b derived by the position fluctuation calculator 21. In the first embodiment, since the positions of the magnetic detectors 6e to 6h fixed on the fixing members 7a and 7b do not fluctuate, the device coordinates calibrating unit 22 calibrates the position coordinates of the magnetic detectors 6a to 6d based on the fluctuation amount of the position of the fixing member 7b relative to the fixing member 7a. The device coordinates calibrating unit 22 also has the function of outputting results of calibration of the positions of the magnetic detectors 6a to 6d to the storage unit 23.

The storage unit 23 stores information necessary to derive the fluctuation amount of the positional relation by the position fluctuation calculator 21, for example, the three-dimensional stereomodel formed by the fixing members 7a and 7b and the distance measuring members 9a to 9f when the subject 1 holds the basic posture, and information necessary for coordinate calibration by the device coordinates calibrating unit 22, for example, the positional relations among the magnetic detectors 6a to 6d. The storage unit 23 also has the function of storing information regarding the position coordinates of the magnetic detectors 6a to 6d used at the time of deriving the position of the test capsule 2 by the position calculator 19.

Figure 8:
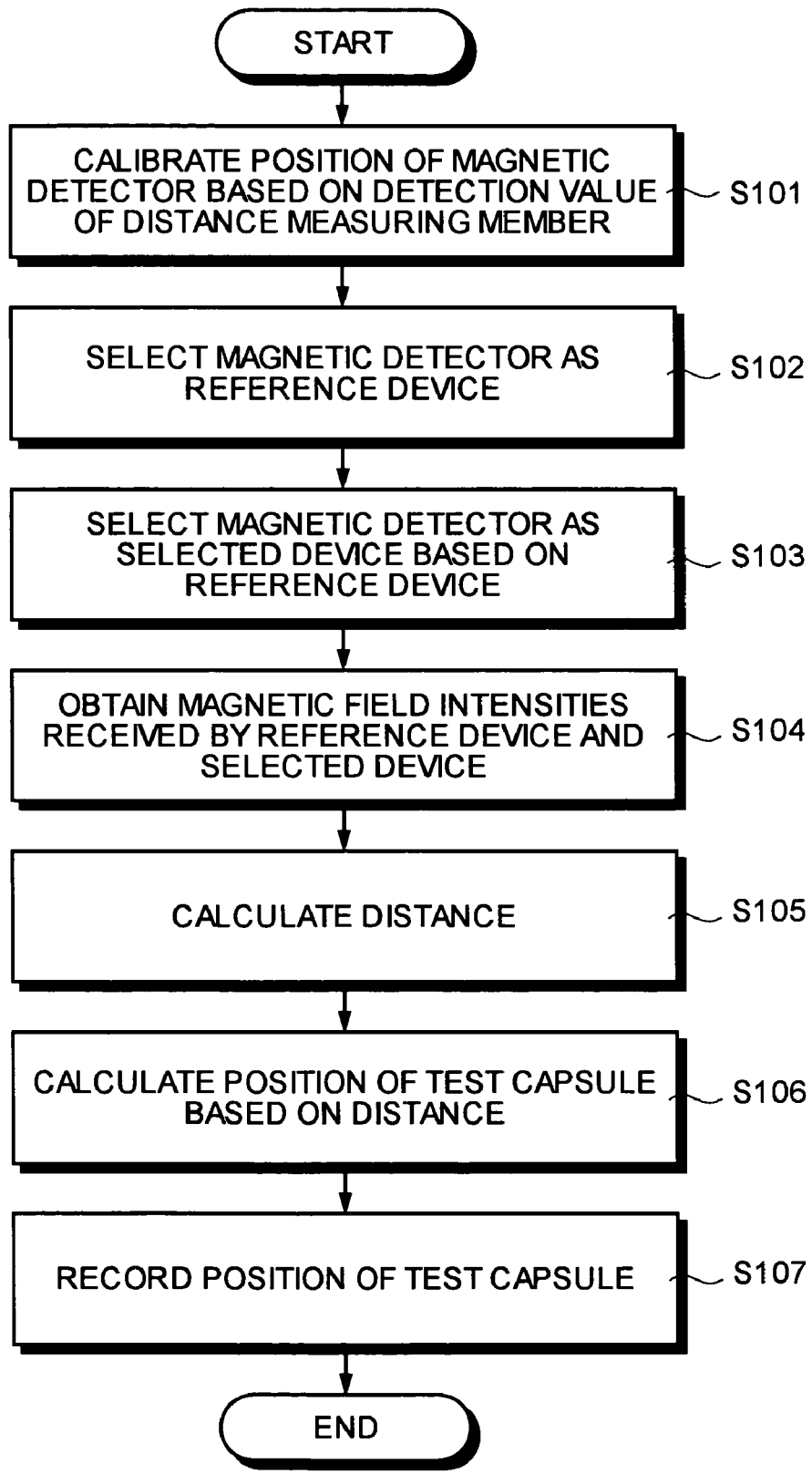
FIG. 8 is a flowchart of operations of the position processor.
Figure 9:
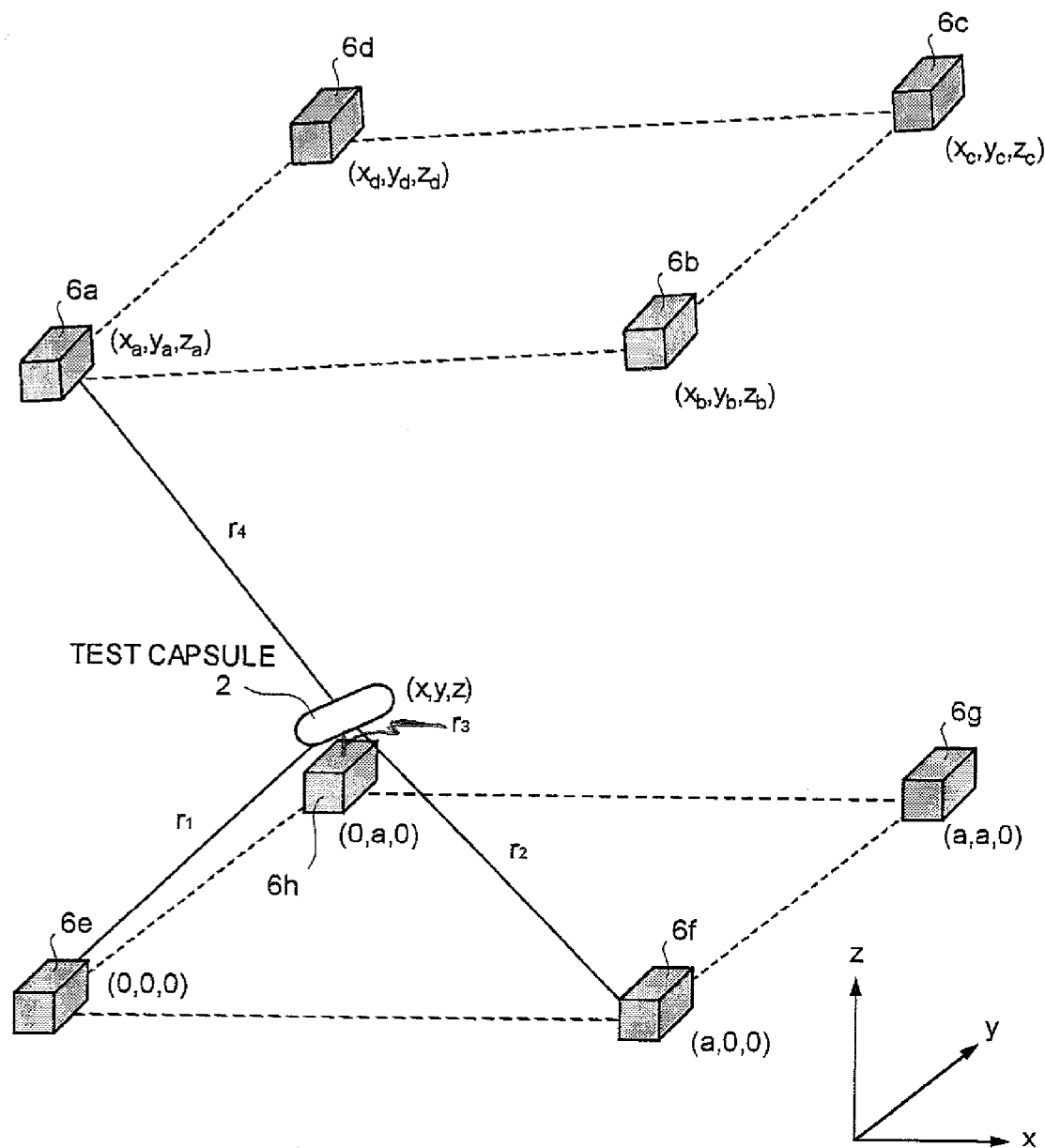
FIG. 9 is a schematic view of calculating the position of a test capsule by the position processor.

The operation of the position processor 8 in the first embodiment is explained. FIG. 8 is a flowchart that depicts the operation of the position processor 8, and FIG. 9 is a schematic diagram for explaining the algorithm of the position calculation. In FIG. 9, the length of one side of a cube constructed by the magnetic detectors 6a to 6h is set as "a". As is explained later, the position of the magnetic detector 6e selected as a reference device is set as the origin, the direction from the magnetic detector 6e toward the magnetic detector 6f is set as an x direction, the direction from the magnetic detector 6e toward the magnetic detector 6h is set as a y direction, and the direction from the magnetic detector 6e toward the magnetic detector 6a is set as a z direction. The positions of the magnetic detectors 6a to 6h are determined based on the xyz coordinate system, and the position of the test capsule 2 in the xyz coordinate system is expressed as (x, y, z). The operation of the position processor 8 is explained hereinbelow by properly referring to FIGS. 8 and 9.

First, the position processor 8 calibrates the position coordinates of the magnetic detectors 6a to 6d by the device coordinates calibrating unit 22 (step S101). Concretely, first, the fluctuation value of the distance between the predetermined points on the fixing members 7a and 7b is detected by the distance measuring members 9a to 9f and, based on the detected fluctuation value and necessary information, the fluctuation amount of the positional relation between the fixing members 7a and 7b is derived by the position fluctuation calculator 21. The device coordinates calibrating unit 22 performs a computing process based on the fluctuation amount and the necessary information to thereby calibrate the position coordinates in the xyz coordinate system of the magnetic detectors 6a to 6d. In the example of FIG. 9, by calibrating the position coordinates, the positions of the magnetic detectors 6a to 6d are derived as $(x_a, y_a, z_a)$, $(x_b, y_b, z_b)$, $(x_c, y_c, z_c)$, and $(x_d, y_d, z_d)$, respectively.

After that, the position processor 8 selects the magnetic detector having the magnetic field intensity that is the highest among the magnetic field intensities received by the magnetic detectors 6a to 6h (step S102). The example of FIG. 9 is a case where the magnetic detector 6e is selected as the magnetic detector detecting the highest magnetic field intensity. In the following description, it is also assumed that the magnetic detector 6e is the reference device.

The position processor 8 selects three devices by the magnetic selector 17 based on the reference device selected in step S102 (step S103), and outputs the magnetic field intensities obtained by the reference device and the selected devices to the distance calculator 18 (step S104). In the example of FIG. 9, the magnetic detectors 6f, 6h, and 6a are disposed in the directions orthogonal to each other with respect to the magnetic detector 6e as a reference device, so that the magnetic selector 17 selects the magnetic detectors 6f, 6h, and 6a as selected devices.

After that, the position processor 8 calculates the distance from the test capsule 2 based on the magnetic field intensity obtained by the reference device selected in step S102 and the magnetic field intensities obtained by the devices selected in step S103 by the distance calculator 18 (step S105). Concretely, the distance calculator 18 calculates the distance by performing computation of Equation (1) using the magnetic field intensity input via the magnetic selector 17. In the example of FIG. 9, the distance calculator 18 calculates distances $r_1$, $r_2$, $r_3$, and $r_4$ between the test capsule 2 and the magnetic detectors 6e, 6f, 6h, and 6a, respectively, based on the magnetic field intensities detected by the reference device and the selected devices.

The position processor 8 calculates the position of the test capsule 2 by the computing process in the position calculator 19 (step S106). Concretely, the position of the test capsule 2 is calculated by deriving the x coordinate, y coordinate, and z coordinate of the test capsule 2, so that the coordinates of the test capsule 2 are derived by using the coordinates of the magnetic detectors 6e, 6f, 6b, and 6a and the values of distances derived in step S105.

For example, the position coordinates (x, y, z) of the test capsule 2 can be geometrically derived from the positional relations shown in FIG. 9 and, concretely, can be calculated by solving the following equations.

$$(x-0)^2+(y-0)^2+(z-0)^2=r_1^2 \quad (2)$$

$$(x-a)^2+(y-0)^2+(z-0)^2=r_2^2 \quad (3)$$

$$(x-0)^2+(y-a)^2+(z-0)^2=r_3^2 \quad (4)$$

In Equations (2) to (5), "a" is a known value, $x_a$, $x_b$, $y_a$, $y_b$, $z_a$, and $z_b$ are derived at step S101, $r_1$ to $r_4$ are derived at step S105, and the number of unknown letters is three so that three equations are theoretically sufficient. At the time of actual position detection, however, to suppress deterioration in precision of the position detection of the test capsule 2 due to a distance derivation error or the like, the values of $r_1$ to $r_4$ and the like are corrected so that the values x, y, and z are unconditionally determined at the time of solving Equations (2) to (5).

Finally, the position processor 8 stores the position of the test capsule 2 calculated in step S106 by the storage unit 20 (step S107). Concretely, while the test capsule 2 is swallowed in the subject 1, the portable recording medium 5 is inserted in the storage unit 20, so that the storage unit 20 records the position information obtained in step S106 into the portable recording medium 5.

The processes in steps S101 to S107 are repeatedly performed at predetermined time intervals. As a result, the portable recording medium 5 records information of travel in the subject 1 of the test capsule 2. After the test capsule 2 is excreted to the outside of the subject 1, the portable recording medium 5 is inserted to the display 4. The user grasps how the test capsule 2 travels in the subject 1 based on the result of recording displayed on the display 4 and determines the location of a narrow region existing in the subject 1 or the like from the grasped result.

The advantages of the system according to the first embodiment is explained. First, the system according to the first embodiment calculates the position of the test capsule 2 based on the constant magnetic field output from the permanent magnet 11 in the test capsule 2. Different from electromagnetic waves and the like, the constant magnetic field has a characteristic that its intensity attenuates almost unconditionally irrespective of physical parameters such as dielectric constant, magnetic permeability, and the like in a propagation region, so that the relation of Equation (1) is excellently satisfied. Therefore, the system has an advantage such that position detection can be performed with higher precision even in a space like the inside of a human body where organs and the like whose physical parameters are different from each other exist as compared with position detection using electromagnetic waves or the like.

Another advantage of using the constant magnetic field is that burden on the subject when the test capsule 2 is introduced into the subject 1 is lessened. For the above reasons, the system according to the first embodiment has an advantage such that deterioration in precision of the position detection due to variations of environments around the test capsule 2 is suppressed. Consequently, for example, at the time of introducing the test capsule 2 into the subject 1, it is unnecessary to impose limitations such as restriction on eating and drinking like in other inspecting methods. Therefore, the subject 1 can live normal life also at the time of an inspection using the test capsule 2 and the burden on the subject 1 in the inspection can be lessened. The system for detecting a position of a device in a subject according to the first embodiment has a configuration that the positions of the magnetic detectors 6a to 6d are calibrated. With such a configuration, in the system for detecting a position in a subject according to the first embodiment, even when the positional relation of the fixing member 7a relative to the fixing member 7b fluctuates due to a motion such as a change in the posture of the subject 1 and the positions of the magnetic detectors 6a to 6d fluctuate, the position of the test capsule 2 can be accurately derived.

The system for detecting a position in a subject according to the first embodiment has the distance measuring members 9a to 9f that detect the distance fluctuation value between the fixing member 7a as a first fixing unit and the fixing member 7b as a second fixing unit, detects a fluctuation in the positional relation between the fixing members 7a and 7b accompanying the motion or the like of the subject 1 based on the distance fluctuation value derived by the elements, and calibrates the positions of the magnetic detectors 6a to 6d based on the detection result. With the configuration, as shown also in FIGS. 5 and 6, the kind and the degree of the motion of the subject 1 can be detected, and position calibration can be performed based on the detection result.

SECOND EMBODIMENT

A system for detecting a position of a capsule endoscope in a subject according to a second embodiment will now be explained. The system according to the second embodiment includes a capsule endoscope, as a device swallowed and passing through a subject, including not only the constant magnetic field generator but also a predetermined function executing unit and a radio unit; and a position processor for switching a plurality of antennas for receiving radio signals transmitted from the capsule endoscope based on the constant magnetic field generated by constant magnetic field generator and the result of detection of the position of the capsule endoscope in the subject as well as the direction of the longitudinal axis of the capsule endoscope, in other words, the orientation direction of the capsule endoscope.

Figure 10:
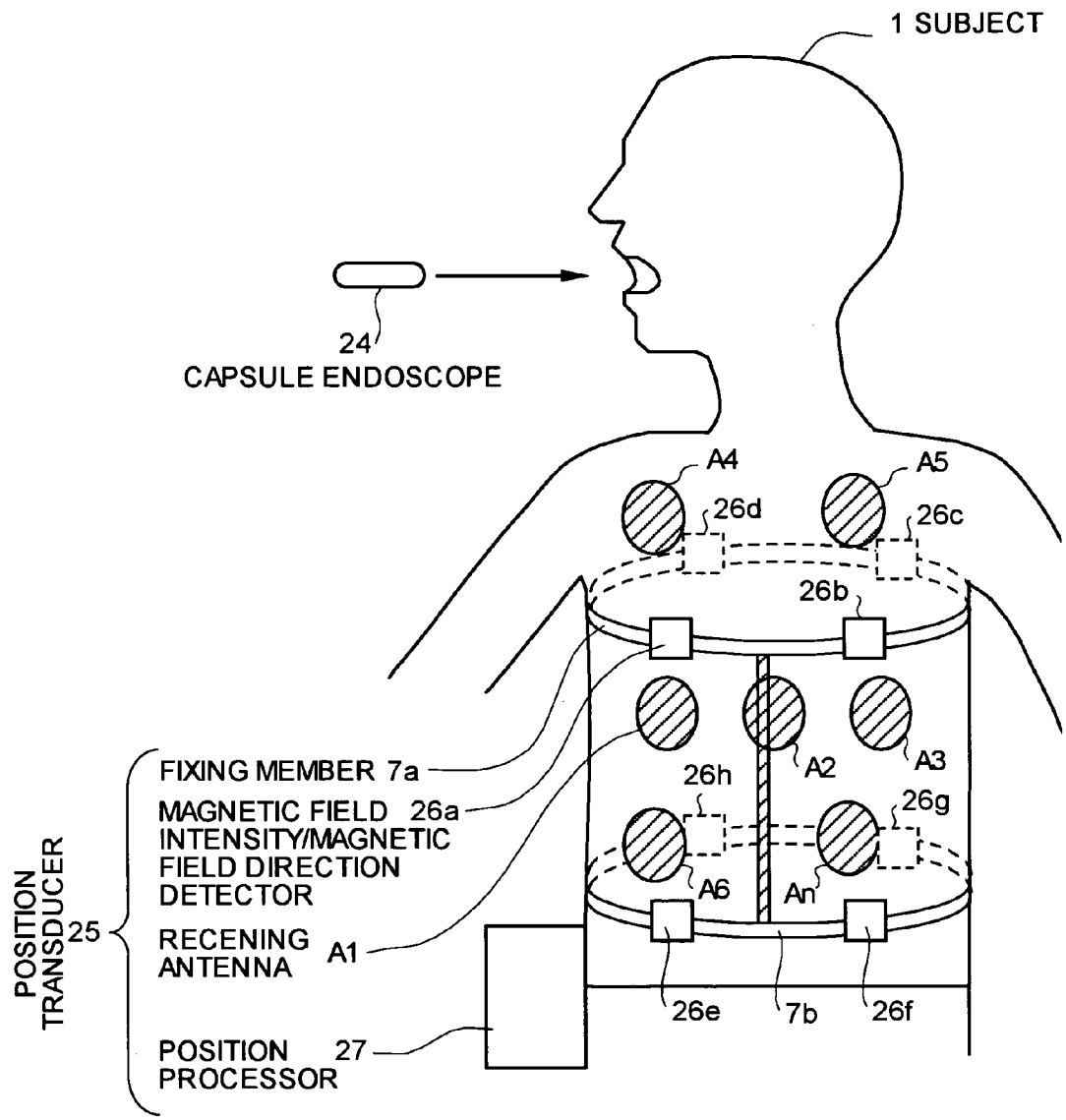
FIG. 10 is a schematic view of a system for detecting a position of a capsule endoscope in a subject according to a second embodiment.

FIG. 10 is a schematic diagram of the system according to the second embodiment. As shown in FIG. 10, the system according to the second embodiment includes a capsule endoscope 24 as an example of the device to be swallowed and passes through a subject, and a position transducer 25. Although elements corresponding to the display 4 and the portable recording medium 5 in the first embodiment are not shown in FIG. 10, it does not mean that those elements are excluded in the second embodiment. In the system according to the second embodiment, elements having the same reference numerals and names as those of the first embodiment have the same configurations and actions as those of the first embodiment unless otherwise specified in the following.

The position transducer 25 includes, as shown in FIG. 10, the magnetic field intensity/direction detectors 26a to 26h, fixing members 7a and 7b for fixing the magnetic field intensity/direction detectors 26a to 26h to the subject 1, receiving antennas $A_1$ to $A_n$ for receiving radio signals transmitted from the capsule endoscope 24, and a position processor 27 for processing the information obtained by the magnetic filed intensity/direction detector 26a to 26h and the receiving antennas $A_1$ to $A_n$ and deriving information of the position in the subject 1, of the capsule endoscope 24.

The magnetic field intensity/magnetic field direction detectors 26a to 26h are for detecting magnetic field intensities and magnetic field directions in positions in which they are located, respectively. Specifically, the magnetic field intensity/magnetic field direction detectors 26a to 26h are formed by MI sensors or the like with functions of detecting magnetic field intensity and magnetic field direction. In the magnetic detectors 6a to 6h according to the first embodiment, only the magnetic field intensity output from the device in the subject is detected, whereas, in the second embodiment, not only the position of the device (capsule endoscope 24) but also the orientation direction thereof is detected, in other words, not only the magnetic field intensity but also the magnetic field direction is detected.

The receiving antennas $A_1$ to $A_n$ are to receive radio signals transmitted from the capsule endoscope 24. As is explained later, the capsule endoscope 24 in the second embodiment has the function of capturing an image of the inside of the subject 1 and transmitting the image to the outside by radio. The receiving antennas $A_1$ to $A_n$ have the configuration of receiving a radio signal transmitted from the capsule endoscope 24 and outputting it to the position processor 27. The receiving antennas A1 to An are constructed by, concretely, for example, a loop antenna and a fixing unit that fixes the loop antenna to the subject 1. When radio signals are transmitted from the capsule endoscope 24, the radio signals may be received by all of the receiving antennas $A_1$ to $A_n$. However, in the second embodiment, the radio signal is received by using a receiving antenna that is determined to be most adapted to reception by an antenna selector 50 that is explained later among the plurality of receiving antennas $A_1$ to $A_n$.

Figure 11:
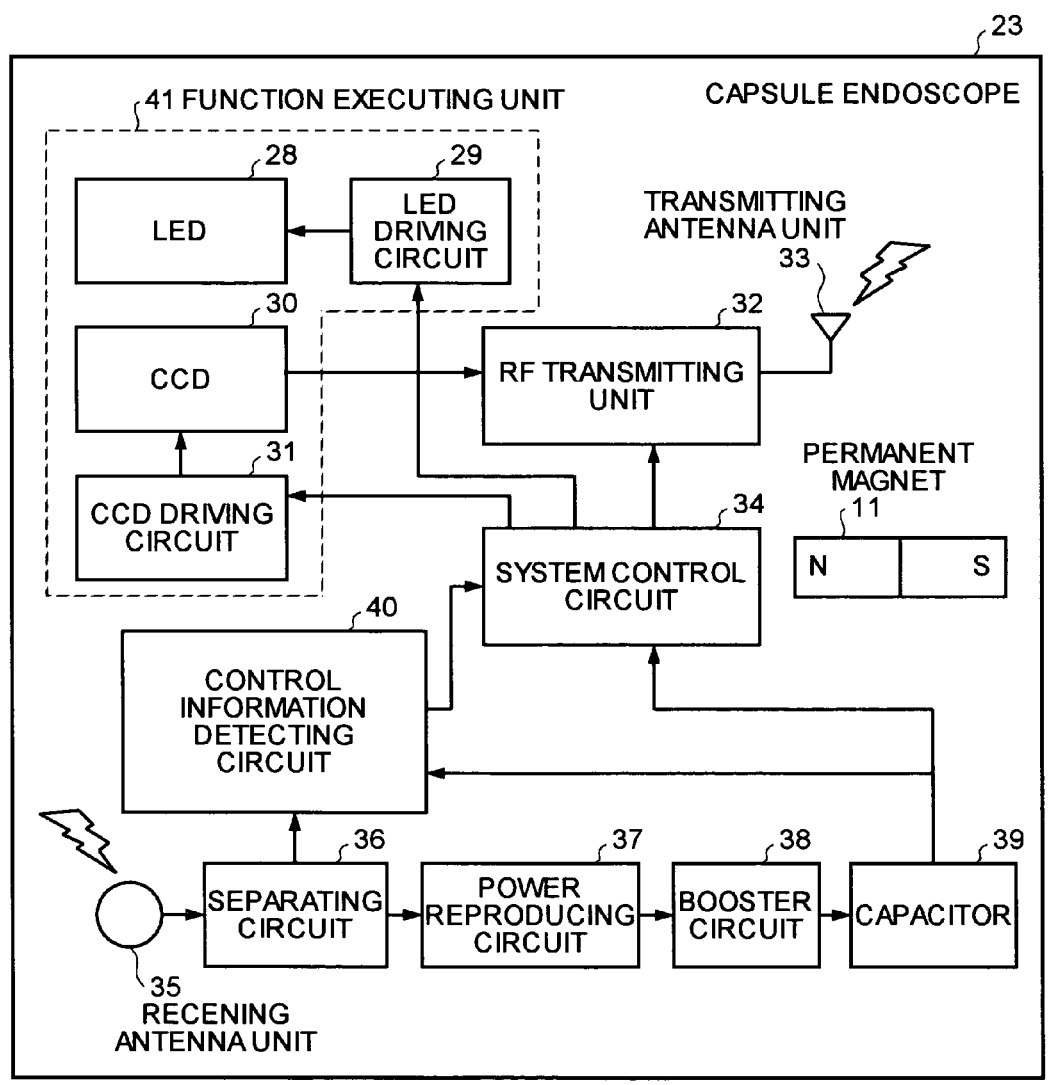
FIG. 11 is a schematic view of the capsule endoscope as a component of the system according to the second embodiment.

FIG. 11 is a block diagram of the capsule endoscope 24. The capsule endoscope 24 has, like the test capsule 2 in the first embodiment, the permanent magnet 11 as the constant magnetic field generator. Further, the capsule endoscope 24 includes a light emitting diode (LED) 28 functioning as a illuminating unit that illuminates an image capturing region at the time of capturing an image of the inside of the subject 1; an LED driving circuit 29 that controls a driving state of the LED 28; a charge-coupled device (CCD) 30 functioning as an image capturing unit for capturing a reflection light image from the region illuminated by the LED 28; and a CCD driving circuit 31 that controls a driving state of the CCD 30. The LED 28, LED driving circuit 29, CCD 30, and CCD driving circuit 31 are defined as a function executing unit 41 having a predetermined function as a whole.

The capsule endoscope 24 includes an RF transmitting unit 32 that modulates image data captured by the CCD 30, thereby generating an RF signal; a transmitting antenna unit 33 as a radio unit for transmitting the RF signal output from the RF transmitting unit 32 by radio; and a system control circuit 34 for controlling the operation of the LED driving circuit 29, CCD driving circuit 31, and RF transmitting unit 32.

By having the mechanisms, the capsule endoscope 24 obtains image data of a region to be tested that is illuminated by the LED 28 by the CCD 30 while the capsule endoscope 24 is introduced in the subject 1. The captured image data is converted to an RF signal by the RF transmitting unit 32 and, after that, the RF signal is transmitted to the outside via the transmitting antenna unit 33.

The capsule endoscope 24 also includes a receiving antenna unit 35 for receiving a radio signal sent from the position transducer 25 side; and a separating circuit 36 for separating the power supply signal from the signal received by the receiving antenna unit 35. The capsule endoscope 24 also includes a power reproducing circuit 37 for reproducing power from the separated power supply signal; a booster circuit 38 for boosting the reproduced power; and a capacitor 39 for storing the boosted power. The capsule endoscope 24 also includes a control information detecting circuit 40 for detecting a control information signal from the components separated from the power supply signal by the separating circuit 36 and outputting the detected control information signal to the system control circuit 34. The system control circuit 34 also includes the function of distributing drive power supplied from the capacitor 39 to the other elements.

By having the mechanisms, first, the capsule endoscope 24 receives the radio signal sent from the position transducer 25 side by the receiving antenna unit 35 and separates the power supply signal and the control information signal from the received radio signal by the separating circuit 36. The control information signal separated by the separating circuit 36 is output to the system control circuit 34 via the control information detecting circuit 40 and used for driving and controlling the LED 28, CCD 30, and RF transmitting unit 32. On the other hand, the power supply signal is reproduced as power by the power reproducing circuit 37. The potential of the reproduced power is boosted to potential adapted to the capacitor 39 by the booster circuit 38, and the boosted potential is stored in the capacitor 39.

Figure 12:
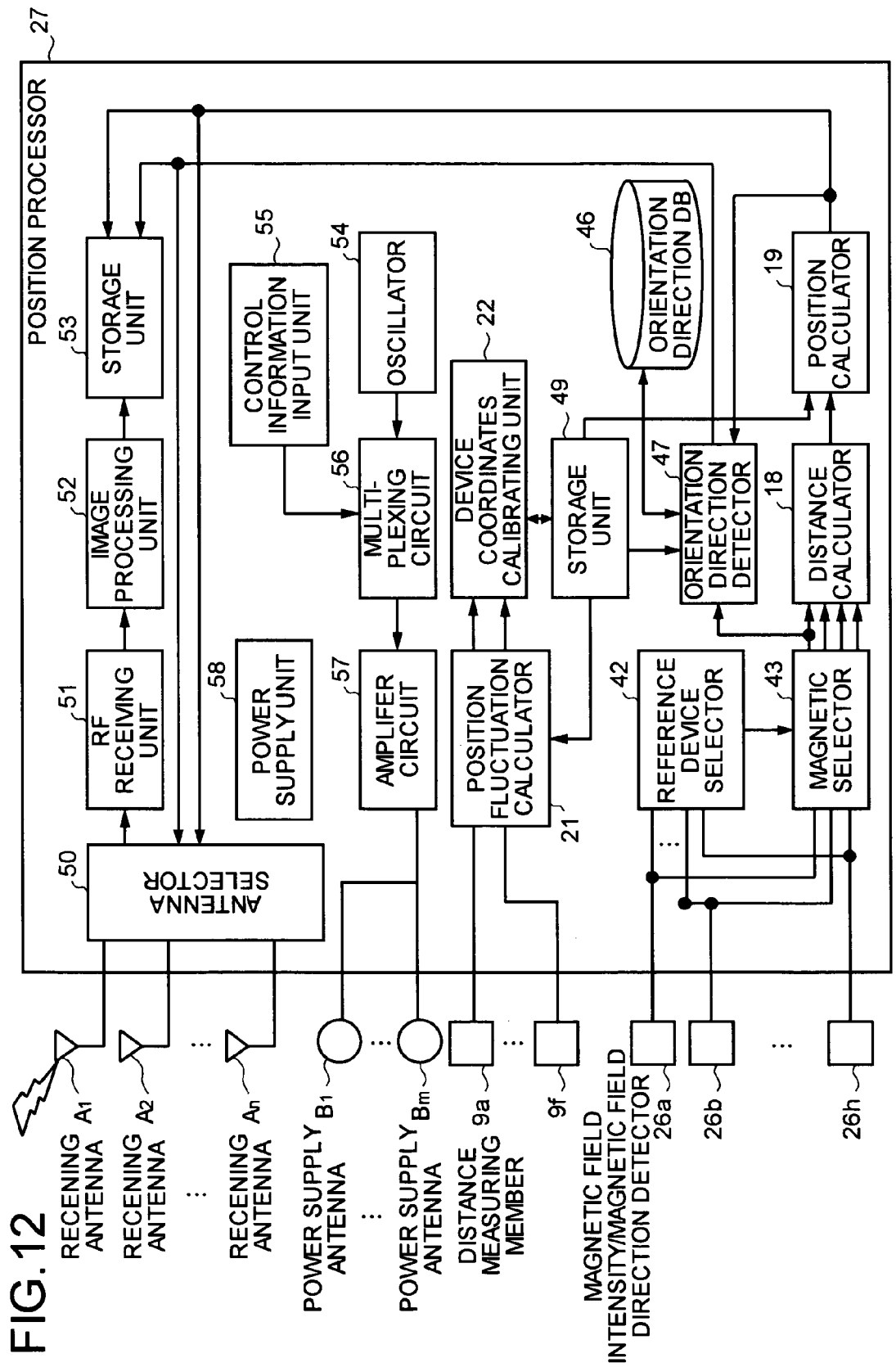
FIG. 12 is a schematic view of a position processor as a component of the system according to the second embodiment.

The configuration of the position processor 27 is explained. FIG. 12 is a block diagram of the position processor 27. The position processor 27 in the second embodiment has, as elements for detecting the position in the subject 1 of the capsule endoscope 24, the reference device selector 42, magnetic selector 43, distance calculator 18, and position calculator 19. In the second embodiment, the magnetic field intensity/magnetic field direction detectors 26a to 26h output not only the magnetic field intensity but also the magnetic field direction to the position processor 27, so that the second embodiment is different from the first embodiment with respect to the following points. The reference device selector 42 extracts the magnetic field intensity from the information output from the magnetic detectors 26a to 26h to select a reference device, and the distance calculator 18 has the function of deriving distance by extracting the magnetic field intensities received by the reference device and the selected devices from the information input from the magnetic selector 43. The operation of detecting the position of the capsule endoscope 24 in the second embodiment is almost the same as that in the first embodiment and its detailed description will not be repeated.

The position processor 27 also has: in a manner similar to the first embodiment, the position fluctuation calculator 21 that derives the position fluctuation amount between the fixing members 7a and 7b based on results of detection of the distance measuring members 9a to 9f; the device coordinates calibrating unit 22 that calibrates the positions of the magnetic field intensity/magnetic field direction detectors 26a to 26d based on the result of derivation of the position fluctuation calculator 21; and a storage unit 49. The operations of the components are almost similar to those in the first embodiment, so that the detailed description will not be repeated.

Furthermore, the position processor 27 includes an orientation direction database 46 used when detecting the orientation direction of the capsule endoscope 24 as described below, and an orientation direction detector 47 that detects the orientation direction of the capsule endoscope 24 based on the magnetic field direction at a predetermined magnetic field intensity/magnetic field direction detector 26 output from the magnetic selector 43. The orientation direction database 46 stores in advance data on magnetic field intensity received at the magnetic field intensity/magnetic field direction detector 26 and orientation directions relative to the positional relationship between the magnetic field intensity/magnetic field direction detectors 26 and the capsule endoscope 24. The specific operation of the orientation direction database 46 and orientation direction detector 47 will be described later in detail.

The position processor 27 also includes the function of a receiving apparatus for receiving image data of the inside of the subject 1, which is sent from the capsule endoscope 24 by radio. Concretely, the position processor 27 has: the antenna selector 50 for selecting an antenna used for data reception from the receiving antennas $A_1$ to $A_n$; an RF receiving unit 51 that performs a predetermined process such as demodulation on a radio signal received by the selected receiving antenna, extracts image data captured by the capsule endoscope 24 from the radio signal, and outputs the extracted image data; an image processing unit 52 for performing a necessary process on the output image data; and a storage unit 53 for storing the processed image data.

The antenna selector 50 selects the receiving antenna that is most adapted to receive the radio signal transmitted from the capsule endoscope 24. Concretely, the antenna selector 50 grasps the positions of the receiving antennas $A_1$ to $A_n$ in advance and receives information of the position of the capsule endoscope 24 derived by the position calculator 19 and information of the orientation direction of the capsule endoscope 24 derived by the orientation direction detector 47. The antenna selector 50 has the function of selecting a receiving antenna that is estimated to have the most excellent reception sensitivity based on the position and the orientation direction of the capsule endoscope 24 and outputting a radio signal received by the selected receiving antenna to the RF receiving unit 51.

The storage unit 53 has the function of storing image data output from the image processing unit 52 and the position and the orientation direction of the capsule endoscope 24 at the time point the output image data is captured in a state where the image data and the position of the capsule endoscope 24 are associated with each other. The position processor 27 has the configuration of outputting the information obtained by the position calculator 19, orientation direction detector 47, and the image processing unit 52 to the storage unit 53 as also shown in FIG. 12, and the storage unit 53 has the function of storing the information in the associated state. As a result, in the storage unit 53, the image data of a predetermined region in the subject 1 and the position and the orientation direction of the capsule endoscope 24 at the time point the image data is captured is stored in a state where the image data and the position and the orientation direction of the capsule endoscope 24 are associated with each other.

The position processor 27 also has the function of generating a power supply signal and the like transmitted to the capsule endoscope 24 and outputting the power supply signal to the power supply antennas $B_1$ to $B_m$. Concretely, the position processor 27 includes an oscillator 54 having the function of generating a power supply signal and the function of specifying an oscillation frequency; a control information input unit 55 that generates a control information signal for controlling the drive state of the capsule endoscope 24; a multiplexing circuit 56 for combining the power supply signal and the control information signal; and an amplifier circuit 57 for amplifying the intensity of the combined signal. The signal amplified by the amplifier circuit 57 is sent to the power supply antennas $B_1$ to $B_m$ and transmitted to the capsule endoscope 24. The position processor 27 includes a power supply unit 58 having a predetermined storage, an AC power adapter, or the like, and the elements of the position processor 27 uses the power supplied from the power supply unit 58 as driving energy.

Next, in the system for detecting a position within a subject according to the second embodiment, the significance of detection of the orientation direction of the capsule endoscope 24 and the operation of detecting the orientation direction will be described. As described above, in the system for detecting a position in a subject according to the second embodiment, the capsule endoscope 24 includes a predetermined function executing unit and the information acquired by the function executing unit is wirelessly transmitted to the position transducer 25 side. Accordingly, the position transducer 25 includes plural receiving antennas $A_1$ to $A_n$ for receiving transmitted radio signals and antenna selector 50 selects a receiving antenna most suitable for reception from the plural receiving antennas $A_1$ to $A_n$.

As an algorithm of selecting a receiving antenna most suitable for reception from the plural receiving antennas $A_1$ to $A_n$, first, determination according to the positional relationship with the capsule endoscope 24 can be cited. For example, it is conceivable that, on the assumption that the radio signal transmitted from the capsule endoscope 24 are attenuated according to the distance, the position of the capsule endoscope 24 is derived by a position detection mechanism same as in the first embodiment, and the receiving antenna nearest to the derived position is used.

However, when the radio signals from the capsule endoscope are received, selecting the receiving antenna according to only the positional relationship with the antenna is not necessarily appropriate. That is, the transmitting antenna unit 33 used for radio transmission from the capsule endoscope 24 does not transmit the radio signals toward various directions with uniform intensity, but transmits the radio signals with a certain degree of directivity because the unit is formed by a loop antenna or the like, for example. Therefore, it is preferred that the receiving antenna most suitable for receiving the radio signals transmitted from the capsule endoscope is not determined according to only the positional relationship with the capsule endoscope, but determined in consideration of the directivity of the radio signals transmitted from the transmitting antenna unit 33. Further, since the transmitting antenna unit 33 is fixed within the capsule endoscope 24, it is important to grasp the orientation direction of the capsule endoscope 24 within the subject 1 to detect the orientation direction of the transmitted radio signals. According to such circumstances, in the second embodiment, the orientation direction of the capsule endoscope 24 is detected with not only the mechanism of detecting the position of the capsule endoscope 24 within the subject 1 as in the first embodiment, but with the orientation direction database 46 and the orientation direction detector 47.

Figure 13:
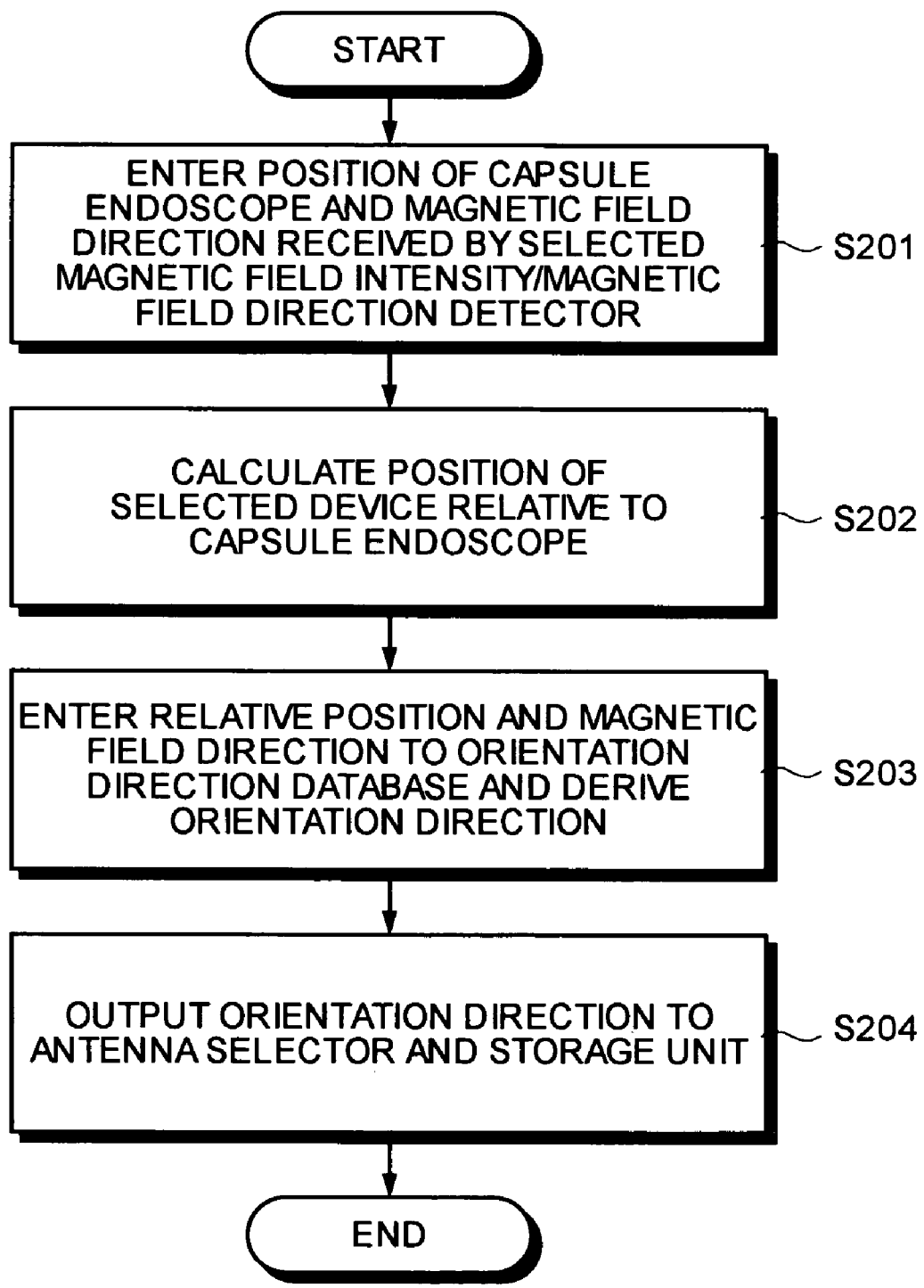
FIG. 13 is a flowchart of operations of the position processor.
Figure 14:
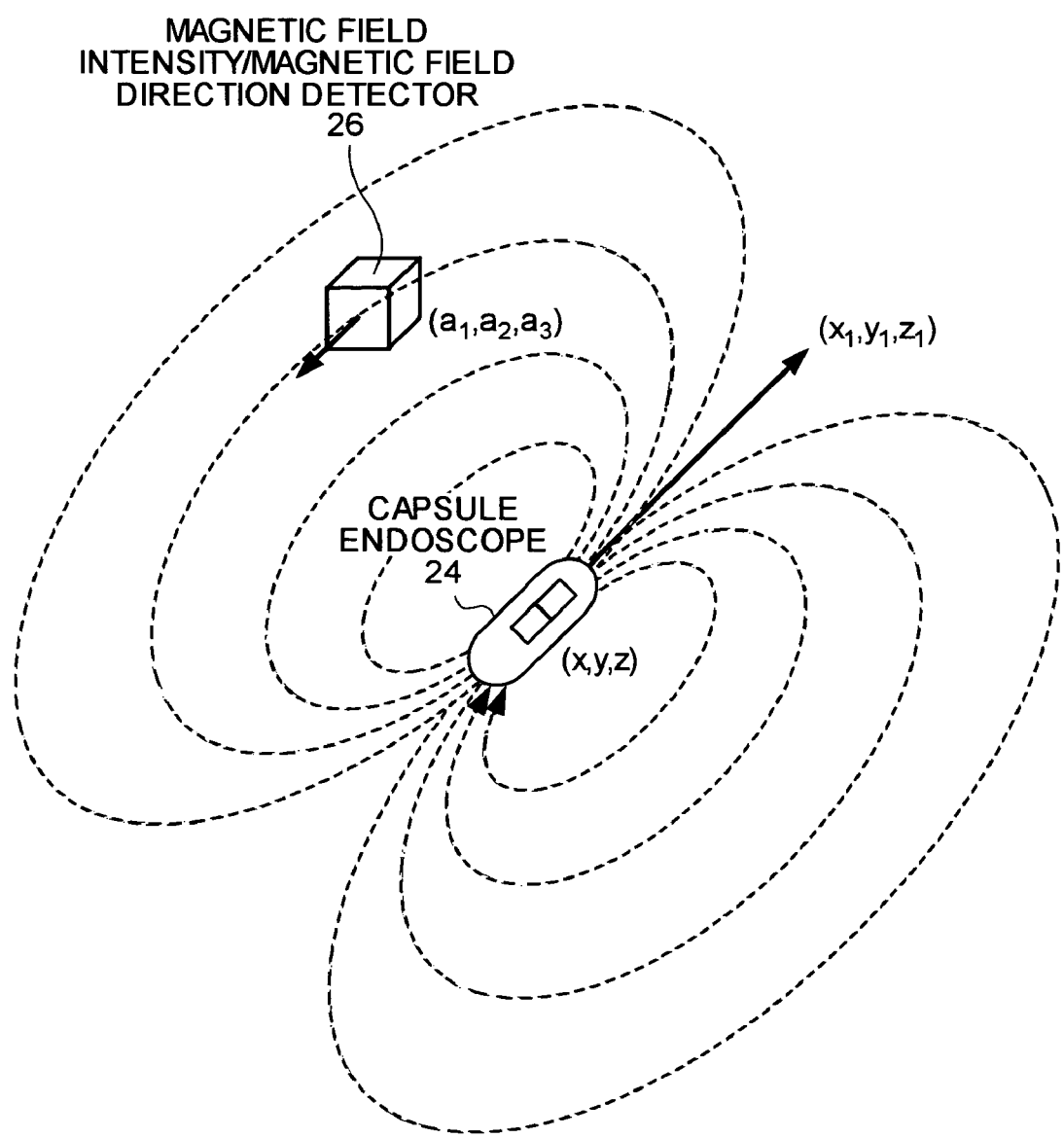
FIG. 14 is a schematic view of calculating the orientation direction of the test capsule by the position processor.

FIG. 13 is a flowchart for explanation of the detection operation of the orientation direction of the capsule endoscope 24 in the orientation direction detector 47 in the second embodiment. Further, FIG. 14 is a diagram that depicts the relationship between the orientation direction of the capsule endoscope and the magnetic field intensity/magnetic field direction detector 26. As below, the operation of the orientation direction detector 47 will be described with reference to FIGS. 13 and 14 as necessary.

First, the orientation direction detector 47 inputs the position of the capsule endoscope 24 and magnetic field direction received by the magnetic field intensity/magnetic field direction detector 26 selected from the magnetic field intensity/magnetic field direction detectors 26a to 26h (step S201). Any selection algorithm may be used for the selection of the magnetic field intensity/magnetic field direction detector 26, and in the second embodiment, the magnetic field intensity/magnetic field direction detector 26 with the largest received magnetic field intensity is selected as an example. In the example of FIG. 14, the orientation direction detector 47 grasps the coordinates $(a_1, a_2, a_3)$ of the selected magnetic field intensity/magnetic field direction detector 26 and the magnetic field direction represented by the direction vector shown by an arrow.

Then, the orientation direction detector 47 calculates the relative position of the magnetic field intensity/magnetic field direction detector 26 selected at step S201 to the capsule endoscope 24 (step S202). Specifically, the position of the capsule endoscope 24 calculated by the position calculator 19 is input to the orientation direction detector 47, and the unit 45 derives the relative coordinates of the magnetic field intensity/magnetic field direction detector 26 selected at step S201 to the capsule endoscope 24. In the example of FIG. 14, the relative position coordinates $(a_1-x, a_2-y, a_3-z)$ of the magnetic field intensity/magnetic field direction detector 26 with the position of the capsule endoscope 24 as a point of origin are derived based on the coordinates $(a_1, a_2, a_3)$ of the magnetic field intensity/magnetic field direction detector 26 and the coordinates $(x, y, z)$ of the capsule endoscope 24.

Then, the orientation direction detector 47 inputs the magnetic field direction input at step S201 and the relative position of the magnetic field intensity/magnetic field direction detector 26 selected at step S202 to the orientation direction database 46 and acquires data on the orientation direction of the capsule endoscope 24 (step S203). As shown in FIG. 14, since the direction of the constant magnetic field output from the permanent magnet 11 provided within the capsule endoscope 24 has a nature which is uniquely determined depending on the orientation direction of the capsule endoscope 24 and the position relative to the capsule endoscope 24, in the orientation direction database 46, the orientation direction of the capsule endoscope 24, the relative coordinates to the capsule endoscope 24, and the directions of the constant magnetic field in the relative coordinates are stored in advance in an associated condition. Accordingly, with the input of the relative coordinates of the magnetic field intensity/magnetic field direction detector 26 and the detected direction of the constant magnetic field to the orientation direction database 46, the orientation direction of the capsule endoscope 24 can be extracted. In the example in FIG. 14, the orientation direction of the capsule endoscope 24 is derived as $(x_1, y_1, z_1)$ based on the output result from the orientation direction database 46.

Finally, the orientation direction detector 47 outputs the acquired data on the orientation direction of the capsule endoscope 24 to the antenna selector 50 and the storage unit 53 (step S204). The antenna selector 50 selects the receiving antenna most suitable for reception based on the data on the orientation direction and the information on the position output from the position calculator 19, and the storage unit 53 stores the orientation direction of the capsule endoscope 24 at a predetermined time in association with the image data and the position information of the capsule endoscope 24.

The advantages of the system according to the second embodiment is explained. First, in the system according to the second embodiment, in a manner similar to the first embodiment, the capsule endoscope 24 includes therein the permanent magnet 11 and the position of the capsule endoscope 24 is detected based on the constant magnetic field output from the permanent magnet 11. As already mentioned above, the constant magnetic field has a characteristic that it attenuates almost unconditionally irrespective of the values such as dielectric constant, magnetic permeability, and the like in organs and the like in the subject 1. Consequently, there is an advantage such that the position of the capsule endoscope 24 can be accurately detected more than the case of performing position detection by using a radio signal.

Further, the system according to the second embodiment has a configuration that the orientation direction of the capsule endoscope 24 is detected based on the constant magnetic field output from the permanent magnet 11. Similarly to the position detection, the constant magnetic field output from the permanent magnet 11 is hardly affected by the component material within the subject 1 and has a property that the magnetic field direction in the predetermined position is nearly uniquely determined based on the orientation direction of the capsule endoscope 24 and the relative position to the capsule endoscope 24. Therefore, when the distribution of orientation of the constant magnetic field output by the permanent magnet 11 is obtained in advance to be stored in the orientation direction database 46, with the reference to the orientation direction database 46 based on the information obtained via magnetic field intensity/magnetic field direction detector 26, the orientation direction of the capsule endoscope 24 can be detected accurately.

Furthermore, since the system according to the second embodiment has the configuration that the orientation direction of the capsule endoscope 24 is detected based on the constant magnetic field similarly to the position detection, the system has an advantage of simple configuration. That is, the system according to the second embodiment does not require addition of new components within the capsule endoscope 24 for realizing the function of detecting the orientation direction of the capsule endoscope 24, whereby the compact and low-cost system can be realized.

The system for detecting a position in a subject according to the second embodiment has a configuration that the antenna selector 50 selects the receiving antenna based on the position and the orientation direction of the derived capsule endoscope 24. The reception sensitivity of the radio signal in the receiving antenna depends on the distance from the capsule endoscope 24 and the orientation of the transmitting antenna unit 33 in the capsule endoscope 24. Therefore, a receiving antenna to be used can be accurately selected based on the position and the orientation direction of the capsule endoscope 24, and a position information detecting system capable of receiving a radio signal transmitted from the capsule endoscope 24 always at high sensitivity can be realized.

Further, the system according to the second embodiment has a configuration of outputting image data of the inside of the subject 1 captured and the derived position and the orientation direction of the capsule endoscope 24 to the storage unit 53. Therefore, image data obtained by the capsule endoscope 24 and the derived position and the orientation direction at the time of image capture of the capsule endoscope 24 can be stored so as to be associated with each other. At the time of displaying image data on the display 4, only the image data positioned in a predetermined range can be designated to be displayed. In other words, every image data is not displayed on the display 4 but image data of a region of interest of the user, for example, image data of only the small intestine can be displayed on the display 4. Thus, the position information detecting system that is convenient to doctors and the like can be realized.

A modification of the system for detecting a position of a device in a subject according to the second embodiment is explained. In the modification, as a position fluctuation detector for detecting a fluctuation state of the positional relation between the fixing members 7a and 7b, in place of the distance measuring members 9a to 9f, an inclination sensor and an azimuth sensor functioning as a mode of the azimuth detector in the claims are used.

Figure 15:
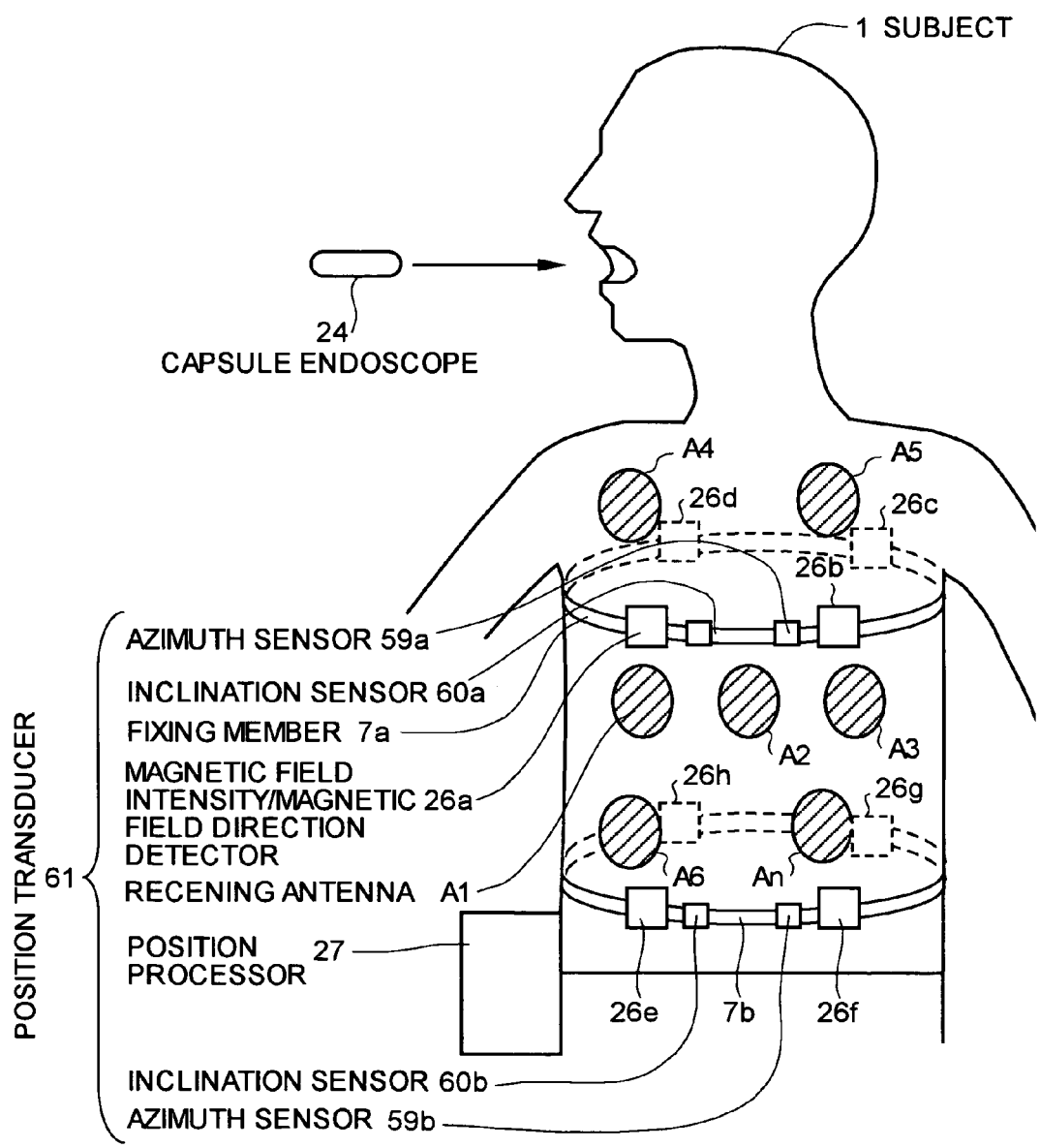
FIG. 15 is a schematic view of a position transducer according to a modification of the second embodiment.

FIG. 15 is a schematic view of the configuration of a position transducer 61 in the modification. As shown in FIG. 15, the modification has a configuration that, in place of the distance measuring members 9a to 9f, an azimuth sensor 5a and an inclination sensor 60a fixed on the fixing member 7a and an azimuth sensor 59b and an inclination sensor 60b fixed on the fixing member 7b are provided.

The azimuth sensors 59a and 59b function as horizontal in-plane azimuth sensors in the claims and have the function of detecting an azimuth in a horizontal plane. Concretely, the azimuth sensors 59a and 59b take the form of gyros or the like and have the function of detecting an angle relative to a predetermined designated direction in a horizontal plane. Since the azimuth sensor 59a is fixed on the fixing member 7a and the azimuth sensor 59b is fixed on the fixing member 7b as described above, by deriving the differential value of the angles relative to the orientation detected by the azimuth sensors 59a and 59b, the difference between the orientations of the fixing members 7a and 7b in a horizontal plane can be detected.

The inclination sensors 60a and 60b function as an inclination sensor in the claims and, concretely, have the function of detecting an angle from the vertical direction. Since the inclination sensor 60a is fixed on the fixing member 7a and the inclination sensor 60b is fixed on the fixing member 7b as described above, by deriving the differential value of the angles from the vertical direction, detected by the inclination sensors 60a and 60b, the difference between the orientations of the fixing members 7a and 7b in the vertical direction can be detected.

The detection of the position fluctuation between the fixing members 7a and 7b by the azimuth sensors 59a and 59b and the inclination sensors 60a and 60b in the modification will be briefly described. As already stated above, as main motions of the subject 1, the bending motion and the twisting motion using the backbone as a rotation axis can be mentioned. The bending motion is realized when the posture of the subject 1 changes in the vertical direction, and the twisting motion can be regarded as a motion that is made in a direction perpendicular to the vertical direction. Therefore, the bending motion can be detected by the inclination sensors 60a and 60b and the twisting motion can be detected by the azimuth sensors 59a and 59b. More concretely, a fluctuation in the positional relation between the fixing members 7a and 7b caused by the bending motion is clarified by deriving the differential value of detection values of the inclination sensors 60a and 60b. A fluctuation in the positional relation between the fixing members 7a and 7b caused by the twisting motion can be clarified by deriving the differential value of detection values of the azimuth sensors 59a and 59b.

Further, in the modification, the position fluctuation calculator 21 is provided with the function of computing a fluctuation amount of the positional relation between the fixing members 7a and 7b based on a change in the orientation, and the storage unit 49 is provided with the function of storing information necessary for the computation. With such a configuration, the system for detecting a movement state in a subject according to the modification can detect the fluctuation amount of the positional relation between the fixing members 7a and 7b based on fluctuation values of the angles from the orientations of the fixing members 7a and 7b and calibrate the position coordinates of the magnetic field intensity/magnetic field direction detectors 26a to 26d based on the detection result.

Although the invention has been described above by the first and second embodiments, the invention is not limited to the foregoing embodiments and various embodiments, modifications, and application examples can be made by those skilled in the art. For example, the system for detecting a position of a device in a subject according to the first embodiment may have a configuration of deriving the orientation of the test capsule 2 in a manner similar to the second embodiment or may employ the configuration of the modification in place of the distance measuring members 9a to 9f of the first embodiment.

Further, though in the first and the second embodiments, a plurality of magnetic detectors 6 and magnetic field intensity/magnetic field direction detectors 26 are each disposed on an outer surface of the subject 1 as to detect an apex of the cube, the disposition of the detectors is not limited to such. With respect to the magnetic detectors 6 and the like, it is sufficient to grasp relative positions to the subject 1 in advance. By using the relative positions, position and orientation direction detection is possible without disposing the magnetic detectors 6 in a cube shape. The number of the magnetic detectors 6 and the like is not limited to eight. As the simplest configuration, a system using a single magnetic detector 6 or the like can be constructed. Specifically, the test capsule 2 or the capsule endoscope 24 as the device to be introduced in the subject does not travel arbitrarily in the subject 1 but travels along a path that is determined to a certain degree of predetermined organs such as esophagus, stomach, small intestine, large intestine, and the like. Therefore, it is possible to preliminarily grasp a travel path of the device to be introduced in a subject to a certain degree. The position of the device to be introduced in a subject can be detected by using the path information grasped in advance and the intensity of the constant magnetic field received by the single magnetic detector.

Further, in the first and second embodiments, the reference device and the selected devices are selected by using the reference device selector 42 and the magnetic selector 17, and position detection is made based on the magnetic field intensities detected by the reference device and the selected devices. The configuration, however, is not essential to the invention. For example, it is also possible to derive the distance from the test capsule 2 or capsule endoscope 24 based on detected intensities with respect to all of the magnetic detectors 6a to 6h and generate eight ways of equations similar to Equations (2) to (5) to derive the position of the test capsule 2 or the like. In the case of the configuration, computation using, for example, the least square method is possible. Thus, there is an advantage such that an error of derivation of the position of the test capsule 2 or the like can be further reduced.

Similarly, in the second embodiment, for example, the orientation direction of the capsule endoscope 24 may be derived via the plural magnetic field intensity/magnetic field direction detectors 26. That is, it is also preferable to derive the orientation direction at the plural magnetic field intensity/magnetic field direction detectors 26 by the above described method and to find the average of the derived orientation directions, to realize more accurate derivation of the orientation direction. Same applies to the detection of the position of the device, for which a plurality of position detections may be performed with the magnetic field intensity detector 6 or the like, and the average of the obtained positions may be found.

Although the function executing unit 41 having the CCD 30 and the like as an image capturing unit and the LED 28 and the like as an illuminating unit has been described in the second embodiment, the function executing unit 41 may obtain, in addition to the above, information of pH and the temperature in the subject 1. A configuration that the device to be introduced in a subject has an oscillator to capture an ultrasonic image of the inside of the subject 1 may be also employed. Further, a plurality of pieces of information may be obtained from the information of the inside of the subject.

The radio signal output from the power supply antennas $B_1$ to $B_m$ is not always limited to a signal obtained by multiplexing the control information signal and the power supply signal. Further, radio transmission from the position transducer to the capsule endoscope may not be performed. The power supply signal and a signal other than the control information signal may be multiplexed and the resultant signal may be transmitted. The position transducer 25 may receive only the radio signal output from the capsule endoscope. It is also possible to provide a storage unit in the capsule endoscope and, after the capsule endoscope is excreted to the outside of the subject, read information from the storage unit.

Further, in the second embodiment, the selection of the power supply antennas $B_1$ to $B_m$ has not been referred to particularly, however, as with the receiving antennas $A_1$ to $A_n$, the most suitable one may be selected based on the position and orientation direction of the capsule endoscope 24 to perform radio transmission. That is, in order to improve the supply efficiency of power supply signals or the like, not the transmission of radio signals uniformly from all of the power supply antennas, but selection of an antenna in response to the orientation direction or the like of the receiving antenna unit 35 provided within the capsule endoscope 24 can be performed using the orientation direction or the like of the capsule endoscope 24.

Further, in the first and second embodiments, the positions of the magnetic detectors 6e to 6h and the magnetic field intensity/magnetic field direction detectors 26e to 26h may be calibrated. Specifically, although it is assumed in the first and second embodiments that the positions of the magnetic detectors 6e to 6h do not fluctuate, in reality, there is a possibility that the positions may fluctuate according to the posture or the like of the subject 1 like the magnetic detectors 6a to 6d. Even in such a case, when the configuration is adopted where a reference point is set in advance such that no position fluctuation occurs relative to the subject 1, the positions of the magnetic detectors 6e to 6h and the like can be also calibrated.

In the first and second embodiments, the system for detecting a moving state of a device in a subject may be constructed by a simpler configuration obtained by reducing the number of distance measuring devices. Specifically, as motions of the subject 1, the bending motion and the twisting motion can be mentioned. It is easily obviously understood that the bending motion is detected by two distance measuring members for detecting a distance fluctuation value between two different points on the fixing members 7a and 7b with respect to the bending angle and the azimuth in the horizontal plane in which a bending motion occurs. As for the twisting motion, as shown also in FIG. 6, by using distance measuring members like the distance measuring members 9c and 9d disposed so as to detect a distance fluctuation value with respect to straight paths that are not parallel to each other, the direction of twisting motion and the angle of twisting motion can be detected. Therefore, as a simple configuration, a fluctuation state of the positional relation between the fixing members 7a and 7b can be detected by, for example, the distance measuring members 9a and 9c in FIG. 3.

Further, the configuration of the distance measuring members 9a to 9f is not limited to that shown in FIG. 4. There are various known mechanisms for detecting a distance fluctuation value between predetermined two points. It is also possible to apply the mechanisms to the first and second embodiments to form a system for detecting a position in a subject. For example, the distance measuring members 9a to 9f may be constructed by a conductive coil that can be expanded in the longitudinal direction and a mechanism for measuring the self inductance of the conductive coil. Specifically, the value of the self inductance of the conductive coil changes in association with the expanding/contracting operations, by detecting an amount of change in the self inductance, a distance fluctuation value can be detected.

As is clear from the foregoing, the system according to the present invention is useful in connection with the swallowable capsule endoscope employed for the medical treatment, and particularly suitable for a device to be introduced into a subject, such as a patient, for the position detection.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A system comprising:
    a device that is swallowed, passed through a subject, and includes a magnetic field generator generating a constant magnetic field; and
    a position transducer that includes
    a first fixing unit that fixes at least a first magnetic detector to the subject,
    a second fixing unit that fixes at least second and third magnetic detectors to the subject, the first, second, and third magnetic detectors each detecting an intensity of the magnetic field, position coordinates of the second magnetic detector and the third magnetic detector being fixed with respect to each other,
    a position fluctuation detector that includes a distance measuring unit and a position fluctuation calculator, the distance measuring unit having a mechanism of detecting a range of variation in a length of the distance measuring unit so as to detect a distance fluctuation between a predetermined point on the first fixing unit and a predetermined point on the second fixing unit, the position fluctuation calculator calculating a fluctuation amount of the positional relation between the first magnetic detector and at least one of the second magnetic detector and the third magnetic detector based on the distance fluctuation detected by the distance measuring unit,
    a coordinate calibrating unit that calibrates position coordinate of the first magnetic detector based on a detection result by the position fluctuation detector, and
    a position processor that calculates a position of the device in the subject based on the intensity of the constant magnetic field detected by at least the first, second, and third magnetic detectors and based on at least the position coordinates of the first, second, and third magnetic detectors after the calibration of the position coordinate of the first magnetic detector by the coordinate calibrating unit.

2. The system according to claim 1, wherein the position fluctuation detector includes a plurality of distance measuring units that detect a distance fluctuation between a predetermined point on the first fixing unit and a predetermined point on the second fixing unit, and
    the plurality of distance measuring units detect the distance fluctuation along a plurality of straight paths that are nonparallel to each other.

3. The system according to claim 1, wherein the position fluctuation detector includes
    an azimuth detector that detects a fluctuation of an angle formed by orientation of the first fixing unit and orientation of the second fixing unit, and
    a position fluctuation calculator that calculates a fluctuation amount of the positional relation between the first and the second magnetic detectors based on the fluctuation of the angle detected by the azimuth detector.

4. The system according to claim 3, wherein the azimuth detector includes an inclination sensor that detects a fluctuation of an angle in a vertical direction, and a horizontal in-plane azimuth sensor that detects a fluctuation of an angle in a horizontal direction, the sensors being provided on each of the first and second fixing units.

5. The system according to claim 1, wherein the position processor calculates a distance between the device and each of the magnetic detectors based on intensities of magnetic field components detected by the magnetic detectors, and calculates a position of the device in the subject based on the calculated distances.

6. The system according to claim 1, wherein the magnetic field generator is disposed in a position where a direction of the constant magnetic filed is fixed,
    the magnetic detectors detect the direction of the constant magnetic field, and
    the position transducer further includes an orientation direction detector detecting an orientation direction of the device in the subject based on the direction detected by the magnetic detectors.

7. The system according to claim 6, wherein the position transducer further includes an orientation direction database that stores, in advance, a relation between a distance from the magnetic field generator, a direction of the constant magnetic field, and an orientation direction of the device in the subject, and
    the orientation direction detector detects the orientation direction of the device in the subject using the orientation direction database.

8. The system according to claim 1, wherein the device further includes a predetermined function executing unit that obtains information of the inside of the subject, and a radio transmitting unit that transmits the information of the inside of the subject with radio communication, and
    the position transducer further includes a receiving unit tat receives a radio signal transmitted from the radio transmitting unit.

9. The system according to claim 8, wherein the position transducer includes the plurality of receiving units that receive a radio signal transmitted from the radio transmitting unit, and
    the position transducer further includes an orientation direction detector detecting an orientation direction of the device in the subject based on a travel direction of the constant magnetic field detected by the magnetic detectors, and a selector selecting the receiving unit used for receiving the radio signal based on the position calculated by the position processor and the orientation direction detected by the orientation direction detector.

10. The system according to claim 8, wherein the function executing unit includes an illuminating unit that illuminates an inside of the subject, and an image capturing unit that captures an image of a region illuminated by the illuminating unit.

11. The system according to claim 10, wherein the position transducer further includes a storage unit that stores an image captured by the image capturing unit and the position of the device at when the image is captured, so that the image and the position are associated with each other.

12. The system according to claim 1, wherein the device is a capsule endoscope.

13. The system according to claim 1, wherein
    the position fluctuation detector includes an expandable conductive coil and an inductance detector measuring a self-inductance of the conductive coil, and
    the distance measuring unit detects the distance fluctuation between the predetermined point on the first fixing unit and the predetermined point on the second fixing unit based on the self inductance measured by the inductance detector.

* * * * *